United States Patent [19]

Karwoski et al.

[11] Patent Number: 5,114,416
[45] Date of Patent: May 19, 1992

[54] FLUID RECOVERY SYSTEM HAVING AN IMPROVED FLOAT VALVE

[75] Inventors: Theodore Karwoski, Hollis; Steve A. Herweck; Steve Vail, both of Nashua, all of N.H.

[73] Assignee: Atrium Medical Corporation, Hollis, N.H.

[21] Appl. No.: 556,022

[22] Filed: Jul. 20, 1990

[51] Int. Cl.⁵ .............................................. A61M 1/00
[52] U.S. Cl. ..................... 604/321; 604/317; 604/320
[58] Field of Search ............... 604/317, 320, 321, 319, 604/4

[56] References Cited

U.S. PATENT DOCUMENTS

| | | | |
|---|---|---|---|
| 3,559,647 | 2/1971 | Bidwell et al. | 604/321 |
| 3,683,913 | 8/1972 | Kurtz et al. | 128/276 |
| 3,993,067 | 11/1976 | Schachet et al. | 604/4 |
| 4,112,948 | 9/1978 | Kurtz et al. | 604/321 |
| 4,465,483 | 8/1984 | Weilbacher | 604/317 |
| 4,540,413 | 9/1985 | Russo | 604/320 |
| 4,655,740 | 4/1987 | Rühland | 604/320 X |
| 4,781,707 | 11/1988 | Boehringer et al. | 604/317 |

FOREIGN PATENT DOCUMENTS 0096579 12/1983 European Pat. Off. ............ 604/321

OTHER PUBLICATIONS

Pamphlet "Thora-Drain III" underwater chest drainage system Chesebraugh-Ponds Inc. 8 pages.

Primary Examiner—Alan Cannon
Assistant Examiner—Elizabeth M. Bueke
Attorney, Agent, or Firm—Lahive & Cockfield

[57] ABSTRACT

A thoracic cavity drainage device includes a first vessel having a plurality of chambers one of which is a regulated drainage chamber, and a separate transfer vessel which receives fluid collected in the drainage chamber of the first vessel. The chambers of both vessels are interconnected in a series by fluid passageways which cooperate to maintain a uniform range of suction in the drainage chamber while preventing passage of water into the drainage chamber and permitting a different level of suction in the transfer vessel. This operation is effective despite relatively large pressure and vacuum impulses caused by stripping of drainage lines, patient coughing, and the like, and despite discrete changes in the physical configuration of the system caused by disconnection of the transfer vessel, connection of the transfer vessel to an infusion line or the opening or closing of fluid lines and ports. A novel transfer vessel empties the drainage device and provides gravity reinfusion of the collected fluids. A mechanism within the transfer vessel provides an effective suction without vacuum connections or pressure regulating adjustments. An improved valve assembly allows a patient to generate the vacuum required for normal inspiration but prevents automatically, a patient from being exposed to dangerously excessive vacuum for an extended period of time.

40 Claims, 14 Drawing Sheets

TIME IN SECONDS UNTIL VALVE RELEASES AT -60 cmH₂O VACUUM PRESSURE

FLUID RECOVERY SYSTEM HAVING AN IMPROVED FLOAT VALVE

BACKGROUND OF THE INVENTION

This invention relates to drainage apparatus, and more particularly to apparatus for draining fluids such as blood from a body cavity and for the reuse of such fluids. The invention is especially concerned with such an apparatus that will allow a patient to generate the required vacuum for inspiration but that will automatically protect a patient from being exposed to dangerously high vacuum levels.

Blood recovered from a patient's body cavity (autologous blood) offers significant advantages over blood from other humans (homologous blood). Autologous blood reduces the risk of adverse reactions and transmission of infectious disease, has near normal oxygen carrying capacity and pH, conserves blood supplies, provides a readily available source of compatible blood; and provides cost savings. For these reasons, the practice of reinfusing autologous blood, known as autotransfusion, is expanding rapidly.

Autotransfusion may be used in the emergency room setting to recover blood lost through chest trauma; in the operating room setting to recover blood shed during surgery; or in the intensive care setting to recover shed mediastinal blood following cardiac or other surgery.

Various devices have been developed to drain and collect fluids such as blood from a body cavity for subsequent auto-infusion. The following U.S. Pat. Nos. illustrate prior art developments in drainage and/or auto-infusion devices.

U.S. Pat. No. 3,559,647 Bidwell et al
U.S. Pat. No. 3,683,913 Kurtz et al
U.S. Pat. No. 3,853,128 Kurtz et al
U.S. Pat. No. 4,018,224 Kurtz et al
U.S. Pat. No. 4,112,948 Kurtz et al
U.S. Pat. No. 4,443,220 Hauer et al
U.S. Pat. No. 4,540,413 Russo
U.S. Pat. No. 4,605,400 Kurtz et al In U.S. Pat. No. 3,853,128, for example, there is disclosed a drain apparatus of one piece unitary construction. The device includes a collection chamber for collecting fluids from a body cavity, a water seal chamber for preventing passage of air from the atmosphere into the body cavity, and a manometer chamber for regulating the degree of vacuum in the system. The collection chamber is connected by a thoracotomy tube to the patient's pleural cavity. The device is connected to a suction pump and the amount of liquid in the manometer chamber determines the degree of vacuum imposed. A valve mechanism is provided in the water seal chamber to permit the outflow of gases from the apparatus in the event of a sudden increase in pressure in the device, such as may occur when the patient coughs.

One difficulty encountered with the prior art devices is that no provision is made for autoinfusing simultaneously with draining. A device which would allow autotransfusion simultaneously with draining would have significant advantages over prior art devices, especially in the emergency room and operating room settings. Elimination of time-consuming intervening steps between collection, transfer of blood, and autotransfusion would streamline the autotransfusion tasks of medical personnel and enhance the utility of autotransfusion.

The prior art drainage devices generally cannot be used to simultaneously collect blood from the pleural cavity and autotransfuse, because there is no provision in prior art devices for automatic regulation of negative pressure during autotransfusion. During autotransfusion, as fluid exits the collection chamber, remaining fluid volume drops and pressure negativity increases. It is important to maintain pressure negativity within a relatively narrow range to keep bleeding to a minimum and to prevent damage to intrathoracic tissue. It is also important to maintain pressure negativity within a relatively narrow range in order to prevent water from being siphoned out of the water seal chamber and into the collection chamber. Loss of water in this manner would render the water seal useless as a one way valve for air.

One approach to the solution to this problem is to provide a chamber comprising a collapsable bag whose volume can change as required. See U.S. Pat. No. 4,443,220. Such blood bags may be removed from the drainage device when full and placed on a stand to effect reinfusion, but these devices are incapable of simultaneous drainage and reinfusion. Another approach is to provide a mechanical pressure regulating mechanism in communication with a collection chamber which functions to regulate the subatmospheric pressure in the collection chamber independent of the chamber's effective volume. See U.S. Pat. No. 4,548,413. Such mechanical pressure regulating mechanisms are costly and often unreliable.

The relative underpressures suitable for drainage of the thoracic cavity are in the range of several centimeters of water, representing a pressure difference of well under 0.01 atmospheres. However, the drainage tube from a patient may itself have a significant volume; as a result, the process of "stripping" the tube to clear its lumen by forcing blockages along the tube may introduce substantial fluctuation in pressure into the drainage vessel. Further, the placing of a separate collection vessel in the suction drainage system alters system volume. For these reasons, the combination of known drainage devices with a separate fluid collection chamber for collecting a portion of fluid for reinfusion cannot be expected to maintain a uniform suction at the desired low level. Moreover, known systems for fluid collection are not adapted for simultaneously both draining fluids and transferring the desired fluids into the circulatory system.

While it is necessary to allow the patient to draw as much vacuum pressure as is required during normal and deep inspiration without breaking the water seal, currently available fluid recovery systems allow dangerously high levels of vacuum to accumulate within the patient's chest. This is due to the ratio of water volume at the bottom of the water seal and the valve design at the top of this chamber. In recognizing this extremely dangerous situation designers have added a manual mechanical Push button type valve to the chest drain in order to release accumulated vacuum pressure. Known chest drain systems, therefore, use float valves to maintain high vacuum in the collection chamber and manually operated vents to release high vacuum. There are, however, problems associated with known manual vents.

One problem associated with manual venting of high accumulated vacuum is that because of restrictions in the height of the calibrated water seal column, the operator of the manual vent has no idea how high the vacuum pressure actually is. Additionally the operator will have to visually observe the water seal float valve position and water level, that is the amount of water on top of the valve, and guess at whether or not excess vacuum is present in the system. Then, only if it is known that the patient's chest tubes have been recently stripped or milked, will the operator assume that there is a dangerous level of vacuum. These known manual venting systems do not give any inherent indication that high vacuum is present other than that of the presence of water on top of the float valve.

Another problem with manual venting of excess vacuum is that to alleviate this vacuum the operator must push down on the manual push button atmospheric valve to allow atmospheric pressure to relieve the closed system vacuum. Such a procedure can take the operator anywhere from 30-60 seconds and requires that constant pressure be kept on the manual vent valve. Additionally, the operator must carefully observe and coordinate the level of the water seal with the release of pressure on the manual valve. If the operator does not carefully observe and coordinate the release of pressure on the manual vent, the patient's intrathoracic vacuum could be lowered to a dangerously low level such as atmospheric pressure. Since the purpose of any water seal chest drain system is to restore and maintain a minimum level of vacuum to the patient's chest following surgery, failure to stop manual venting at the proper moment, will cause serious clinical event known as pneumothorax. Such an event will require immediate physician attention.

It is, therefore, an object of the present invention to provide a fluid recovery system having an improved float valve in the water seal chamber that provides automatic controlled release of accumulated high vacuum beyond that required for patient inspiration.

It is also an object of the invention to provide a reliable, easily used, inexpensive, and disposable drainage device capable of simultaneous collection and auto-infusion of collected fluid and which regulates subatmospheric suction pressure during both drainage and auto-infusion while minimizing introduction of ambient air to the collected and reinfused fluids.

It is yet another object of the present invention to provide a versatile device which functions effectively intra-operatively as a suction powered drainage device, as well as post-operatively as a device for draining the plural and mediastinal cavities without inducing excessive bleeding or fluid exudation and without damaging intrathoracic tissue.

SUMMARY OF THE INVENTION

The present invention provides a disposable unitary structure for sterile collection of fluids from the thoracic cavity of a patient, and for simultaneous reinfusing such fluids back to the circulatory system of the patient. The apparatus comprises a rigid collection chamber for receiving fluids from the pleural cavity, a U-shaped water seal chamber for preventing unhindered passage of air from the atmosphere into the body cavity, and optionally a manometer chamber for maintaining a selected subatmospheric pressure range in the collection chamber. In a preferred embodiment the collection chamber has three ports: the first port is adapted for connection to a tube for drawing fluids from the pleural cavity or a wound or opening into the collection chamber; the second port communicates with the water seal chamber; and the third port, controlled by a valve, seal or diaphragm is adapted for connection with an infusion pump or separate reinfusion or transfer vessel for delivering fluids collected in the collection chamber into the circulatory system of the patient.

The various means for maintaining an underpressure condition, such as the water seal and manometer, are each configured to have a relatively broad and continuous response to pressure fluctuations. The device is thereby operable to maintain a selected subatmospheric pressure range in the collection chamber during outflow of collected fluid, and to permit reinfusion of fluids from the collection chamber simultaneously with drainage from the pleural or other body cavity into the collection chamber.

For allowing the patient to draw as much vacuum pressure as is required during normal and deep inspiration, while providing an automatic controlled release of accumulated high vacuum in the collection chamber, the present invention includes an automatically releasing float valve interposed between one arm of the water seal chamber and the collection chamber. By tailoring a specific volume of water for a given size chamber cavity, fluid column, and float valve assembly, the improved float valve is made to release at a precise threshold of accumulated high level of vacuum over a given period of time without nurse intervention. Release of the float valve above the maximum vacuum threshold is directly related to the level of high vacuum pressure. That is, the higher the vacuum, the shorter the time period for valve release.

This design also automatically restores the Patient back to its minimum lower vacuum threshold or "pre-high negative pressure episode" level. Accordingly, in accordance with the system of the present invention, the patient can never experience a hazardous event which will reduce the system's vacuum lower than a minimum safe threshold. This design is not only tamper resistant but safer for the patient and provides a simple automatic release system that does not need to be monitored by an operator.

In a preferred embodiment, the system includes a spring-loaded transfer vessel which connects to the third port to provide a system wherein a single fluid connection adds or removes the transfer vessel. No additional valving, vacuum connections or other connections are required, and the drain line from the patient is not disturbed. Despite the significant changes thereby introduced in local pressure levels and total chamber volume, the desired suction level is maintained and collected fluids are removed from the chamber without interruption or system instability for disposal or reinfusion of the collected fluids.

BRIEF DESCRIPTION OF THE DRAWING

For a fuller understanding of the nature and objects of the invention, reference should be made to the following detailed description and the accompanying drawings, in which

FIG. 4c is a cross-sectional view of the float valve of the present invention, the view being oriented 90° to that of FIG. 4a;

Throughout the description, like reference characters in respective drawn figures indicate corresponding parts.

DESCRIPTION OF ILLUSTRATED EMBODIMENTS

Figure 1:
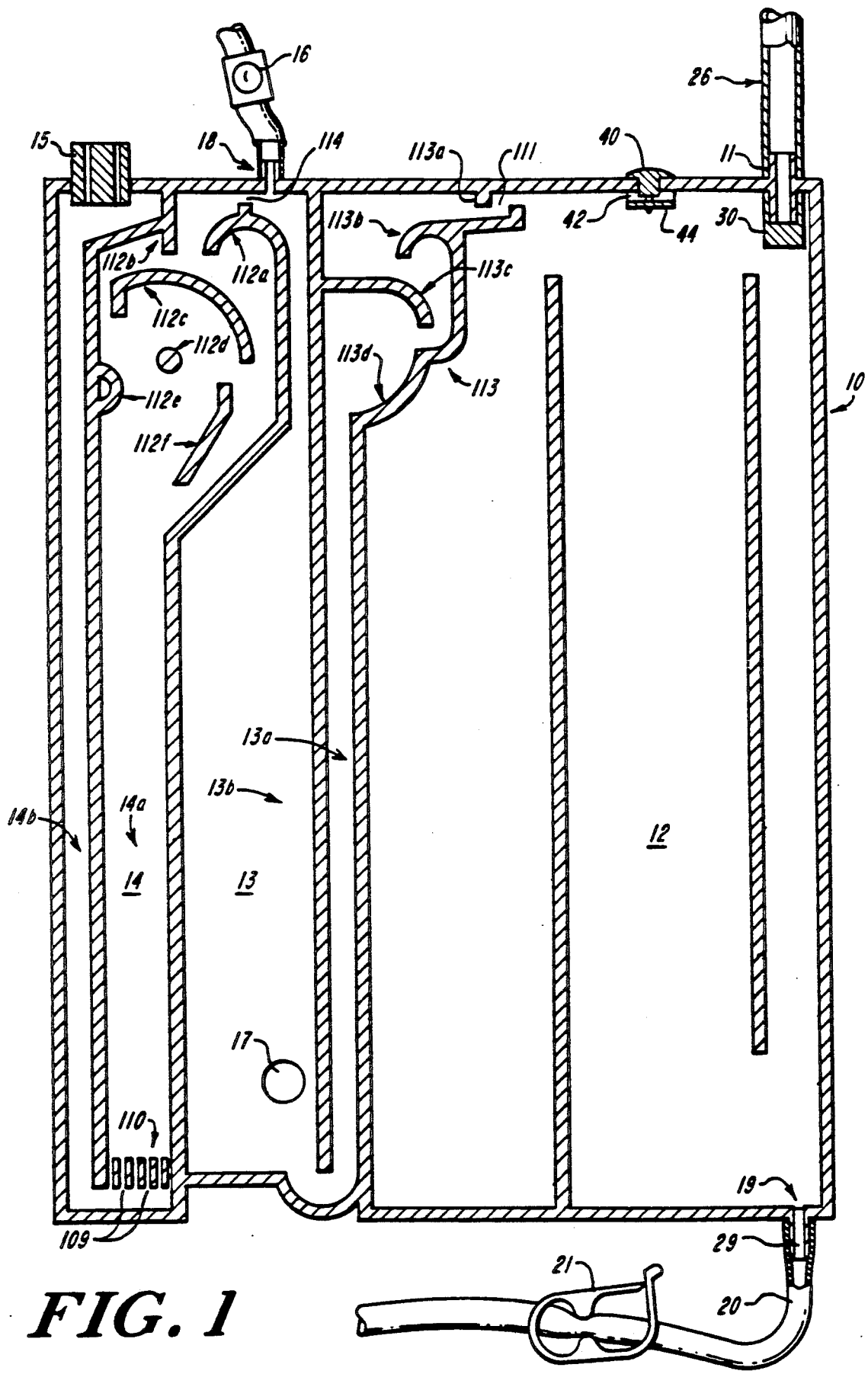
FIG. 1 is a sectional view of a basic drain device according to the invention.

Referring to FIG. 1, there is shown a chest drain device 10 which is preferably of unitary construction, fabricated by adhering together rigid molded parts of plastic, at least some of which, as described in further detail below, are transparent. The device generally comprises a collection chamber 12, a U-shaped water seal chamber 13, and a suction control or manometer chamber 14.

Blood and other fluids from a patient's body cavity enter drain device 10 through a tube 26 attached to inlet port 11, and are collected in collection chamber 12 after passing through a gross filter 30 which traps macroscopic debris such as blood clots, bone fragments, and the like entrained in the incoming fluid. Filter 30 preferably has an approximate pore size of 80-270 microns, suitable for filtration of such contaminants as bone and other tissue not suitable for blood transfusion. Collection chamber 12 is preferably provided with graduated markings (not shown) indicating the volume of fluid it contains.

Water seal chamber 13 provides a barrier to reflux of atmospheric air into a patient's pleural cavity. Water seal chamber 13 is a U-shaped chamber having two arms 13a and 13b, and preferably is provided with grommet 17 for filling with water via a syringe needle. Water seal chamber 13 preferably also has graduations to indicate fill level. Arm 13a of water seal chamber 13 is of smaller cross-sectional area than arm 13b, and communicates with collection chamber 12 via structure 113 and port 111. Disposed at the top of arm 13a of the water seal chamber 13 is an improved automatically releasing float valve 60. The float valve 60 allows the patient to draw high vacuum in the collection chamber 12 for breathing while automatically releasing when an excessive vacuum is maintained for an extended period of time. As will be discussed in greater detail herein below, the float valve 60 enables the system 10 to safely and simultaneously both collect and auto infuse fluid of a patient.

The upper end of arm 13b has a vacuum port 18 for connection to a source of vacuum. Water seal chamber 13 communicates with arm 14a of manometer chamber 14 through port 114. Arm 14b of manometer chamber 14 is vented to the atmosphere through vented plug 15, which is removable to allow filling of manometer chamber 14 with water. Manometer chamber 14 is preferably provided with graduated markings to indicate fill level. Arms 14a and 14b communicate via the narrow slits 109 in bubble indicator 110. The manometer chamber regulates vacuum by allowing air at atmospheric pressure to pass through the manometer water column and bubble indicator into the water seal chamber. The amount of water disposed in manometer chamber 14 serves to regulate the subatmospheric pressure in chambers 12 and 13 generated by the vacuum source attached to port 18. Specifically, when a vacuum source is connected to port 18, the subatmospheric pressure difference in the region of port 114 will be equal to the height in centimeters of the water column in arm 14a, under normal operating conditions.

Certain respiratory conditions can cause a sudden increase in pressure within the pleural cavity. For example, a cough or an air leak into the pleural cavity can produce a substantially higher pressure within the pleural cavity; such pressure must be relieved to permit normal respiratory function. Additionally, such a sudden increase in pressure is passed directly to the drain device by tube 26, and in a prior art device can force water out of the manometer chamber through vented plug 15. This is undesirable, since upon return to lower pressure in the pleural cavity, a substantially lower vacuum will be imposed on the cavity due to the lower remaining water volume in the manometer chamber. The device 10 avoids this problem in part by providing, in addition to the aforesaid port and water column structure, a self-regulating, diaphragm-type, positive pressure release valve 16, located in the vacuum line attached to port 18.

Near the bottom section of collection chamber 12 is disposed a fluid removal port 19. The port includes a microemboli filter 24, preferably a 20-40 micron filter. Tubing 20 is attached to port 19 and is fitted with a conventional clamp 21 which controls the flow of fluid from chamber 12 into an infusion pump 28 (FIG. 2) or transfer/infusion vessel 50 (FIG. 3).

Figure 2:
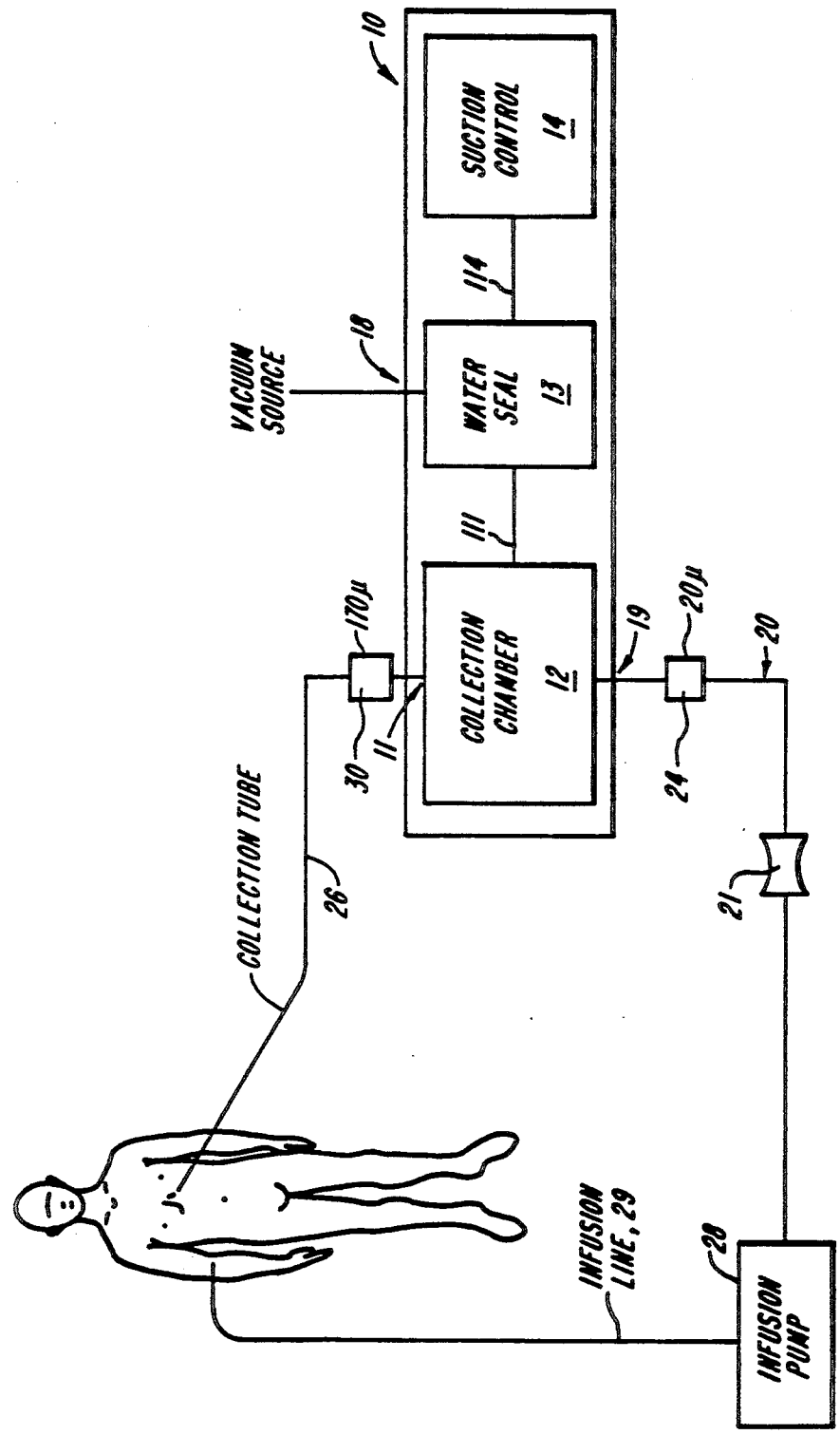
FIG. 2 is a schematic diagram showing an autotransfusion circuit according to the present invention.
Figure 3:
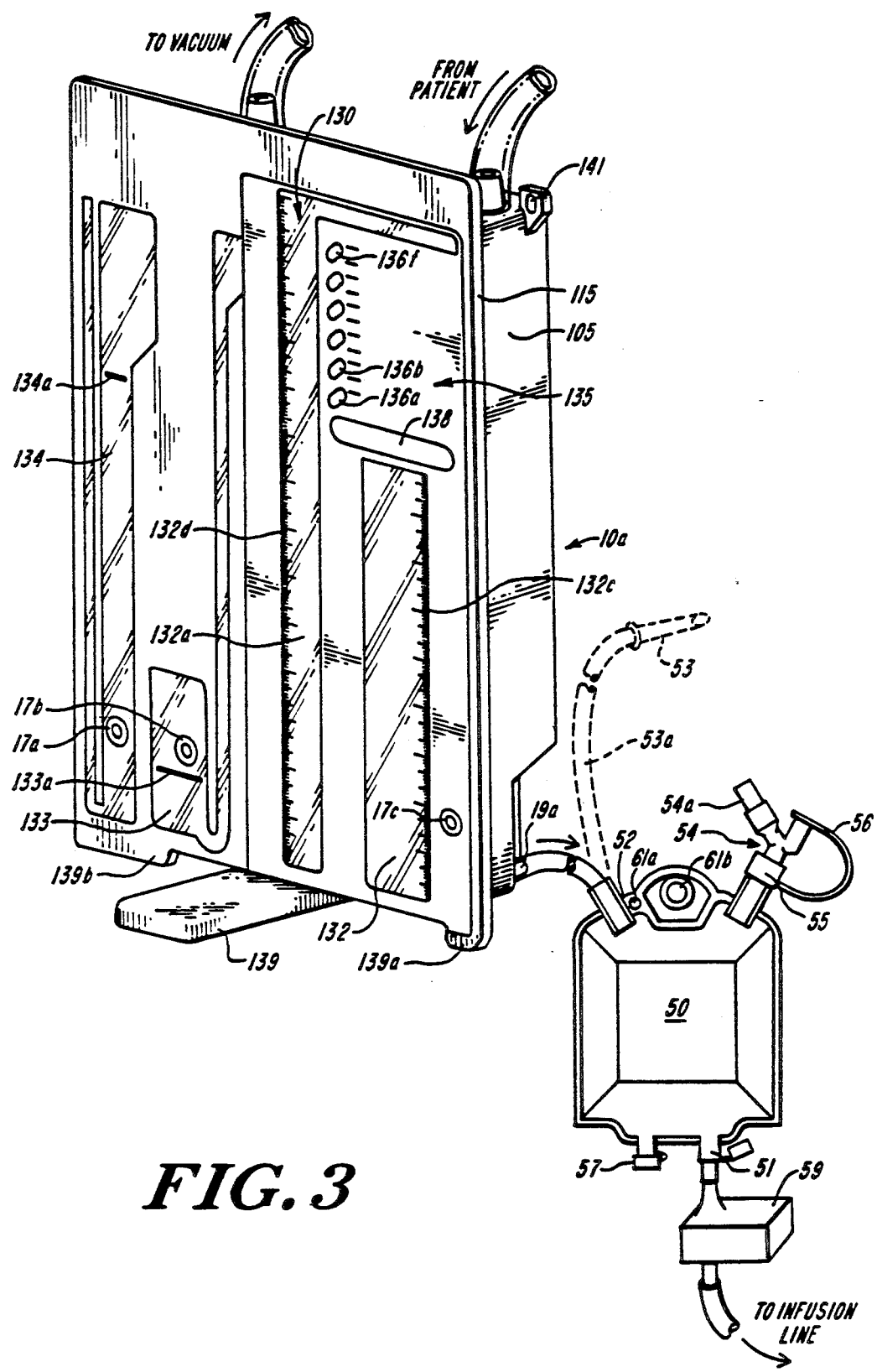
FIG. 3 is a front perspective view of a preferred system for implementing an autotransfusion circuit similar to that of FIG. 2.

Operation of the drain apparatus is best understood with reference to FIG. 2, a schematic of an autotransfusion circuit utilizing the invention. In use, water seal chamber 13 is filled with water to a preselected level, and manometer chamber 14 is filled with water to a level corresponding to a desired subatmospheric pressure. Thoracotomy tube 26 is connected to the patient and to port 11, and vacuum from a wall outlet or portable vacuum source is then applied to vacuum port 18. Vacuum modulated by air bled in through the manometer chamber is thereby applied to the collection chamber 12, and to the thoracotomy tube 26, and fluids such as blood are drawn into collection chamber 12. Such collection may be utilized in the emergency room, operating room, intensive care or other post operative settings.

When used intra-operatively, a conventional suction head (not shown) is sealed to the distal end of tube 26, and the surgeon periodically vacuums the patient's blood from the site of the incision. When used postoperatively, the thoracotomy tube 26 is implanted in a suitable location in the patient's body cavity, typically the pleural cavity, and fluid is withdrawn as it collects while a subatmospheric pressure compatible with normal breathing is maintained in the pleural cavity and in collection chamber 12.

Body fluids entering chamber 12 pass through filter 30 which traps particulate matter, assuring that the liquids collected in chamber 12 are free of macroscopic particles. Irregularities of the pressure in chamber 12 caused by coughing of the patient or "milking" of the thoracotomy tube 26 are accommodated automatically in the device by changes in water levels within the columns 13a, 13b of the water seal chamber 13. Fluctuations in the vacuum source attached to port 18 are modulated by the water in the manometers chamber 14 and positive pressure relief valve 16 which automatically permit influx or reflux of air as required to maintain internal subatmospheric pressure in the narrow range corresponding to the water columns.

In the system of FIG. 2, autotransfusion may be accomplished by opening clamp 21, thus permitting fluid to flow out through filter 24, port 19, along line 20, and into infusion pump 28, which returns fluids to the patient via infusion line 29.

Referring again to FIG. 1, the present invention allows for automatic regulation of negativity during autotransfusion by virtue of the cooperation of port 111 through which water seal chamber 13 communicates with collection chamber 12, elements 113a through 113d of self-bailing structure 113, and the automatically releasing float valve 60. As fluid is autotransfused through port 19, subatmospheric pressure in chambers 12 and 13 as generated by the vacuum source and the egress through port 19 of the fluid from the collection chamber 12 are equalized through port 111 as air passes upwardly through chamber 13a. During normal operation, i.e. when water seal column height is less than approximately 25 cm of H2O, seal integrity is maintained by the structure 113, which prevents interchamber siphoning. Water rising as a column in chamber 13a and entrained as a mist in air bubbles passing through the column is confined in the impound volume 64 defined by valve seat 61 and the structure 113 and returned to the water seal chamber through the aperture 62. Similarly, elements 112a through 112f protect manometer integrity by preventing interchamber siphoning effects between the manometer and water seal chambers.

When, due to either stripping or milking of the tube 26, or due to the suctioning of fluid out of the collection chamber 12 for autotransfusion, there is excessive vacuum in chamber 12 such that the water column in chamber 13a reaches the float valve 60, the float valve 60 will operate to insure that sufficient vacuum is maintained in chamber 12 for an adequate, but not too long period of time. Typically, the float valve 60 will be positioned in the chamber 13a so that a water column of approximately 25 cm activates the float valve 60.

Figure 4B:
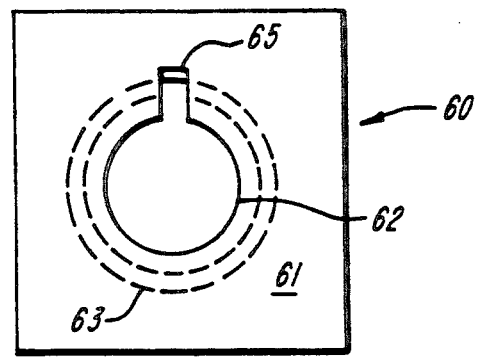
FIG. 4b is a top view of the float valve of the present invention.
Figure 4A:
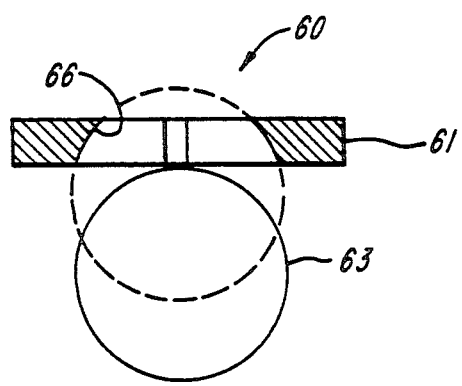
FIG. 4a is an enlarged cross-sectional view of a float valve constructed in accordance with the present invention.
Figure 4C:
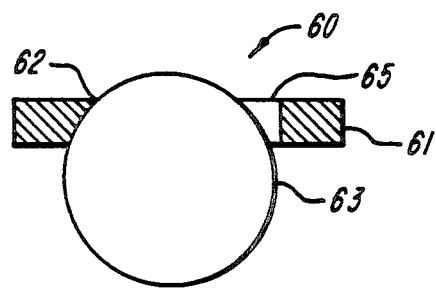

As shown in FIGS. 4a–c the float valve 60 includes a valve seat 61 and a ball 63. While a ball is shown in the figures, floats of other geometrics such as, for example, a cylinder, are equally suitable. The valve seat 61 defines an aperture 62 having an edge 66 which in a preferred embodiment is bevelled. The aperture 62 is shaped so that when it is engaged by the ball 63, water can still pass through but at a substantially reduced rate. Illustratively, the aperture 62 is shaped as a circle in communication with a notch 65. The aperture 62 has a diameter smaller than that of the ball 63 so that when the water level in chamber 13a reaches the float valve 60 the ball 63, having a density of less than one, is buoyantly urged into the aperture 65 and prevents free flow of water into the collection chamber 12.

The beveled edge 66 of the aperture 62 facilitates release of the float valve 60 when the fluid column can no longer support the ball 63. Additionally, by placing the valve seat 61 at a height of 25 cm, higher than is done with known float valves, and using a smaller quantity of water in the water seal chamber 13, an extended period of excessive vacuum causes depletion of the water column by water passing through the aperture 62 and results in the float valve 60 releasing. Accordingly, the float valve 60 accommodates the different fluctuations occurring during simultaneous auto-infusion of fluids and collection of fluids and prevents water siphoning from chamber 13a into the collection chamber 12 during normal pressure fluctuations, further protecting the patient from excessive vacuum by providing automatic release.

Of course, while a float valve is depicted, other valves that permit the free passage of air but impede the passage of water can be used. A porous hydrophobic filter, for example, can be positioned in the chamber 13a so that air, but not water, from chamber 13a freely passes to collection chamber 12. Such a filter would have a cross-sectional area of from approximately 1 cm$^2$ to approximately 20 cm$^2$, depending on the dimensions of chamber 13a, with pores ranging in size from approximately ½ micron to approximately 100 microns. In this manner, as relatively low pressure in collection chamber 12 causes the water column in chamber 13a to rise, air on top of the water column will freely pass into the collection chamber 12. Once the water level reaches the valve, vacuum will be maintained in the collection chamber 12 as the flow of water from the water seal chamber 13 is impeded. Eventually, however, an extended period of excessive vacuum in collection chamber 12 will result in substantially all of the water in the water seal chamber 13 passing through the porous filter and into the collection chamber 12. At this point, air will be allowed to pass freely through the porous filter and into the collection chamber 12.

For intraoperative use, suction can be controlled via a wall outlet regulator, or via manometer chamber 14. In any case, use of the device in this manner provides more gentle suction levels than those attainable by prior art intraoperative drain systems.

When used in this fashion collected fluids can be reinfused on a continuous basis directly back into the patient through filter 24 and infusion pump 28, because the gentle and continuous suction automatically provided by drain 10 is compatible with the simultaneous outflow and inflow of blood from collection chamber 12.

In fact, because of this gentle suction regulation, collected blood may be withdrawn and reinfused in accordance with the invention without use of any electrical infusion pump or other major equipment. FIG. 3 shows such a non-mechanical autologous blood circuit.

A drain unit 10a substantially similar to the device of FIG. 1 has an outlet 19a at the base of its collection chamber 12 to which a transfer vessel 50 is connected to receive fluids collected in chamber 12. Transfer vessel 50 is a heavy plastic bag having an inlet 52, and an outlet 51, as well as a vent 54 having a microporous filter 55 and closure cap 56. Inlet 52 and outlet 51 are at opposed ends of the bag, with the top/bottom orientation defined by a hole 61b for hanging the bag in a vertical orientation. A pierceable sampling or medication injection port 57 is preferably also provided.

At the bottom of vessel 50 a separate microemboli filter 59 is interconnected between port 51 and an infusion line. Shown in phantom is a spike connector 53 and large bore PVC infusion tubing 53a which, in the preferred embodiment, are permanently connected to inlet 52 and adapted to couple with a mating diaphragm closure and spike-compatible connector extending from the outlet port 19a of the drain 10a. Before interconnection of the drain and transfer vessel, connector 53 is maintained in a sterile state in a sheath 54a formed on the vent manifold 54.

Transfer vessel 50 is adapted to generate its own suction, and preferably is a spring-loaded suction vessel, having an internal structure of the type, for example, which is illustrated in U.S. Pat. No. 4,429,643. For purposes of describing the conventional aspects of this vessel, the disclosure of that patent is hereby incorporated herein by reference. That patent shows a bag with an internal folding frame which is urged apart by a coil spring to exert a force on opposite sides of the bag, creating a strong and reasonably uniform suction. An embodiment of that patented spring-loaded suction vessel is presently marketed by the Johnson and Johnson Company as its "J-VAC" suction reservoir. In that device, a folding box-like internal frame placed about a coil spring is normally maintained in a substantially flat position by an internal latch. When the frame is slightly bent, the latch mechanism releases, and opposing walls of the frame are thereafter urged to unfold under the influence of the spring, creating an effective suction of 0.05 to 0.10 atmospheres.

For the practice of this invention, the precise suction level is not important, so long as it is sufficient to overcome the draw of collection chamber 12. An appropriate vessel is achieved by modifying the above-described commercially available suction vessel to further incorporate a capped and filtered vent, a capped outlet port vertically opposed to the vent, and preferably also a sampling port as shown in FIG. 3. In addition, the internal spring is suitably treated to meet USP blood compatability specifications for contacting blood which is to be reinfused, and blood-compatible polymers or coatings are used for the internal frame structure as well as the bag inner surface. For the particular transfer vessel described, the level of suction developed by the vessel, corresponding to a water column of twenty to fifty centimeters, is sufficiently stronger than the levels maintained in drain 10a, to readily draw out any fluids from the collection chamber 12 of the drain. The suction differential remains effective to drain the collector 10a when transfer vessel 50 is suspended at any height approximately level with or below the top of drain 10a.

Operation of the system for collecting fluids and reinfusing the collected fluids proceeds as follows. First, the drain 10a is set up by filling the manometer and water seal chambers to an appropriate level for achieving the desired suction. This level will depend on whether the device is used intra-operatively, or, if post-operatively, on the nature of the thoracic drainage site and whether there is leakage into the thoracic cavity. Next, the vacuum source is connected, and then the drain line to the Patient is connected. During this period, the outlet port is closed, or, if vessel 50 is connected, the port may be open so long as all vents and outlets of vessel 50 are closed and its spring mechanism is latched in the retracted position.

When a sufficient volume of blood for reinfusion has collected, vessel 50, if not already attached, is attached and its spring mechanism released. This draws the collected blood through port 19a from drain 10a into vessel 50.

Thereafter, the line from the drain outlet port is clamped, and vessel 50 is removed and its inlet is closed. The outlet of vessel 50 is then connected through a microemboli filter to an infusion line, and its contents are redelivered to the patient. This may be accomplished by placing a pressure cuff about vessel 50 for bolus delivery. Alternatively, it may be accomplished by hanging the vessel at a suitable height above the patient, opening the filtered vent, and delivering the vessel contents by gravity infusion. Once disconnected, a second vessel 50 may be connected to receive a further unit of collected blood, and to similarly reinfuse the blood.

Returning to the drain 10a of FIG. 3, several features of the preferred embodiment are shown in the front perspective view, and are noted here before proceeding to a more detailed discussion of the interior shape of the preferred drain. Drain 10a is of a multichamber design wherein a unitary housing is formed of two portions. A molded rear or body portion 105 is preferably formed of a light-colored opaque plastic, and contains a number of baffles, walls and posts which extend to a common front plane and define the internal structure of chambers, ribs, ports and supporting elements much as previously discussed in relation to FIG. 1. Front panel 115 is formed of a transparent sheet of substantially uniform thickness. The body portion and the front panel are preferably assembled by linear vibration welding. For this purpose, slight protruding ridges may be formed in the inner face of the front panel to align with and seal to the linear wall portions of the body securely The front panel, as illustrated, has a graphic mask 130 printed thereon defining a plurality of windows, status indicators and calibration or measuring indicators.

Among the "windows" defined by graphic mask 130 are a manometer window 134, a water seal window 133, and a collection chamber window 132, each of which is aligned over the corresponding chamber of the housing. Preferably fill lines 134a, 133a in the windows mark the appropriate water level to achieve a suitable suction level and water seal. In the illustrated embodiment, an additional window 132a is aligned over a second fluid collection column, which as discussed in greater detail below, is preferably at least partially isolated from the normal inlet-filtration-outlet circuit. Each of the windows preferably has a grommet port 17a, 17b, 17c which may be used, in the case of windows 133, 134 to fill or replenish the water column, and in the case of window 132 to sample the collected fluid.

In addition to the aforesaid window structures, the graphic overlay 130 includes an opaque region 135 which, as described in greater detail in regard to FIG. 4, covers a portion of the drain having a large area gross blood filter through which fluids drained from the patient fall to reach the collection chamber Preferably, opaque region 135, or one of the columns or regions below it, certains a printed chart, e.g., a set of blank lines against a light matte ground, to write a schedule of fluid recovery, or a record of fluids transferred to a vessel 50 or to an infusion conduit. In opaque region 135 a series of small clear windows 136a–136f provide an indication of the level of fluid accumulated inside the drain over the gross filter, as described below, of which the general location and shape is indicated at 138. The level indicated by windows 136a–136f depends on the rate of blood collection, and on the volume of accumulated clots. When the level continues to rise, unfiltered blood overflows into the column of window 132b.

A pedestal 139 is rotatably attached to housing 105, and rotates out from the general plane of the drain device to provide, together with face plate protrusions 139a, 139b, a base and stabilizing feet to support the drain upright on a surface. An alternate means of support is to provide hooks from a pair of brackets 141 (of which one is visible in the figure) to hang the drain from a frame.

It will be observed that each of windows 133,134 has a narrow and a wide portion. These portions lie over narrow and wide arms of the respective water columns. Another feature visible in FIG. 3 is that the housing of drain 10a is not of uniform front-to-back depth. For example, it will be seen that outlet 19a is located in a lower portion of the drain having a chamber thickness approximately half that of the upper portion. This geometry of differing chamber depths efficiently channels fluid to a lower collecting sump region. Other localized differences in a chamber depth or thickness, described in greater detail below, cooperate to provide a stable and highly uniform suction drain device.

Figure 5:
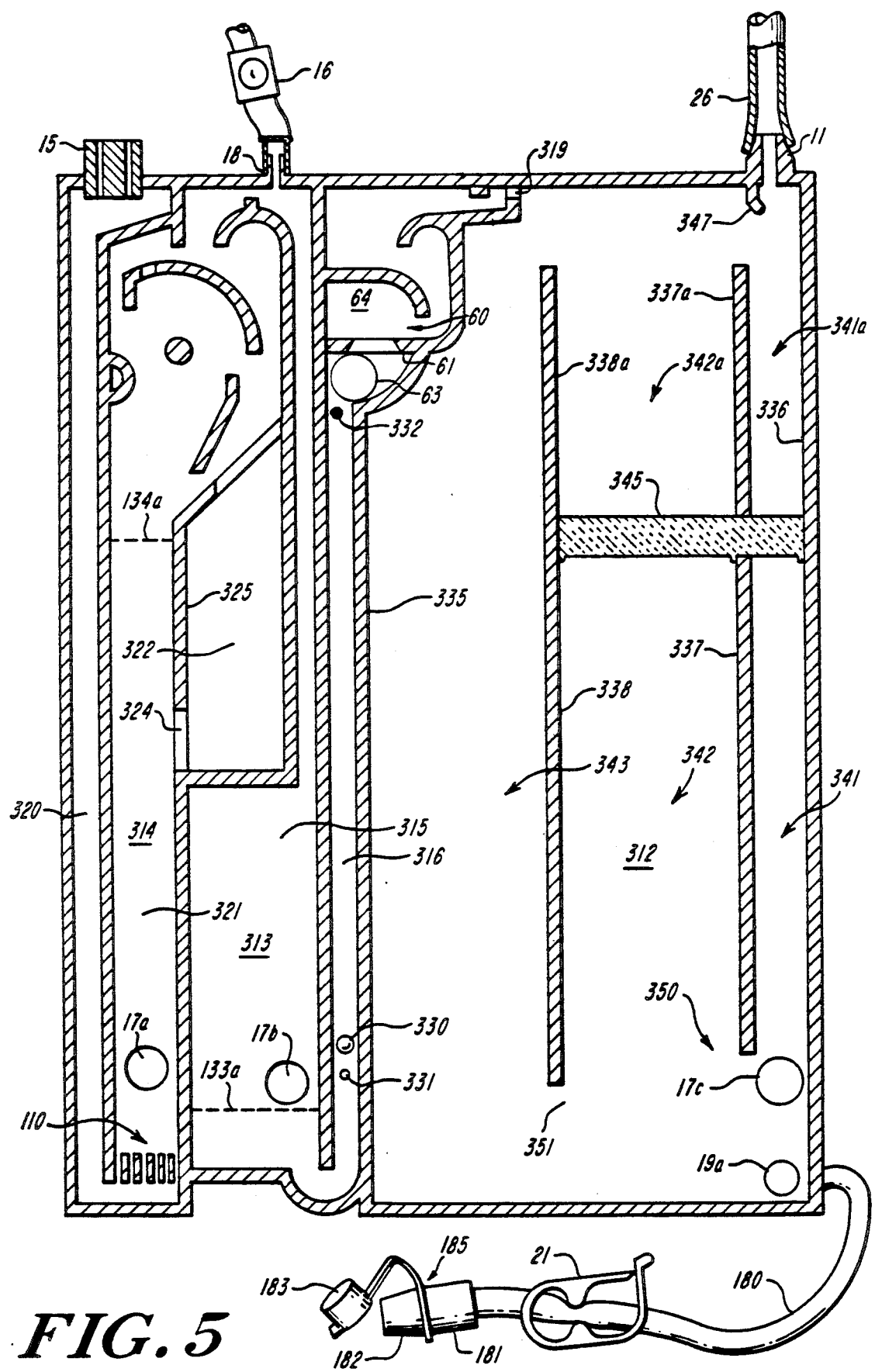
FIG. 5 is a sectional view of the drain device shown in the system of FIG. 3.

FIG. 5 is a sectional view of the molded rear body portion 105 of drain 10a of FIG. 3, taken along a plane parallel to and slightly behind the front panel 115. To aid in visualizing the correspondence with features of FIG. 3, the fill lines 133a, 134a and grommets 17a, 17b, 17c are indicated on the Figure, although they are features of the panel 120. The pierceable sample/fill grommets 17 may alternatively be located in apertures in the rear wall of the body portion 105 in the positions indicated in FIG. 5. Certain details of FIG. 5 are also intended as schematic rather than as exact sections. For example, the level indicating ball 330, described below, is simply shown in a perspective view for emphasis.

Drain 10a, like the basic embodiment of FIG. 1, includes an internal structure of walls which separate the interior into three chambers, namely a manometer chamber 314, a water seal chamber 313, and a fluids collection chamber 312, which are laid out in a series flow path, with the vacuum source connected to port 18 between chambers 314 and 313.

A principal feature of the illustrated device is that it achieves stable and safe suction levels despite changing conditions at the patient inlet port 11, and at the outlet/reinfusion port 19a. To this end, the device includes the float valve 60 as described above and the walls defining the three chambers and the passages therebetween have the following properties.

Manometer chamber 314 includes a two arm U-shaped water column wherein a first arm 320 which is open to the atmosphere via plug 15 has a cross-sectional area substantially below (e.g., less than one tenth) that of the second arm 321 which communicates with vacuum port 18. Such an arrangement limits the amount of water which is drawn from column 320 into column 321 when suction starts, so that the resting height of the water column 321 accurately reflects the intended suction level. It further limits the amount of water which can be blown from column 321 into column 320 in the event of a pressure surge in the interior of the drain, so that short time pressure fluctuations are modulated by the expenditure of energy in pushing water along the column, and abrupt water losses which might disable the device do not occur. A third sub-chamber 322 communicates with arm 321 via lateral opening 324 in a divider wall 325. This sub-chamber effectively doubles the fluid-holding capacity of the manometer chamber, yet is spaced out of the air flow path between the bubble-former 110 and the vacuum port 18, so that water in the sub-chamber is shielded from the evaporative losses due to airflow through chamber 314 which would otherwise regularly degrade the accuracy of the suction setting. This multi-subchamber arrangement stabilizes the suction level over the long term, as well as providing a larger buffer volume to prevent fluid loss from pressure back-surges.

As in the embodiment of FIG. 1, a plurality of curved baffles (not numbered) in the upper portion of the manometer chamber return condensate to the water column.

The volumes of water in the manometer chamber 314 required to achieve a given suction level in a prototype embodiment are set forth in the following table of manometer fill volumes. It will be seen that the relationship between desired suction pressure and required water volume is not linear. That is, higher suction levels require more than proportionately larger volume of water.

TABLE I

| Desired Suction Pressure | Approximate cc Volume |
| --- | --- |
| $-20$ cm $H_2O$ | 320 cc |
| $-15$ | 180 cc |
| $-10$ | 80 cc |
| $-5$ | 38 cc |

The water seal chamber 313 similarly includes a pair of arms of imbalanced cross-sectional area, 315, 316 with the smaller-section arm 316 communicating via a reflux structure 317, a tortuous path 318 and a baffled port 319 with the blood collection chamber 312. As with the arms of the manometer chamber, the smaller arm 316 preferably has a cross-sectional area which is ten percent or less of that of the larger arm 315. At the top of the arm 316, however, the portion of the arm containing the reflux structure is enlarged to define an impound volume 64 above the float valve 60. In the event an extreme underpressure condition should occur in the collection chamber 312, therefore, the fluid from arm 315 which passes through the aperture 62 may be accommodated within arm 316 and will not be drawn through port 319 into the collection chamber.

In the event that an excessive vacuum condition in collection chamber 312 causes a rush of water to be sucked up arm 316 toward port 319, as discussed previously, the water's progress is stayed in large part by the float valve 60. In this manner, extreme pressure fluctuations can be accommodated in the collection chamber without disabling the entire drain device. Water which manages to pass through the float valve 60 is retained in the impound volume 64 and prevented from mixing in the collection chamber 312. If the excessive vacuum condition is maintained in the chamber 312 for an extended period of time, a sufficient quantity of water passes through the float valve 60 to cause the float valve 60 to release thereby relieving the excessive vacuum condition.

A level indicating ball 330 rides in column 316 between two permanent posts 331, 332 formed in body portion 105, so that the level of the float provides an indication of an anomalous underpressure in chamber 312, visible through window 133 (FIG. 3). When an anomalously high suction in the collection chamber causes the level indicating ball 330 to reach the post 332, any additional rise in the water level engages the float valve 60. If the high suction is maintained only for a short period characteristic of patient inspiration, the float valve 60 maintains this high suction in the collection chamber 312. If, however, the high suction is maintained for a dangerous period of time, i.e. longer than a patient breath-interval water passing through the valve 60 reaches the impound volume 64. The weight of this water opens the valve 60 and relieves the suction. Also, the suction is automatically lowered by the passage of air from columns 315, 316.

Figure 6A:
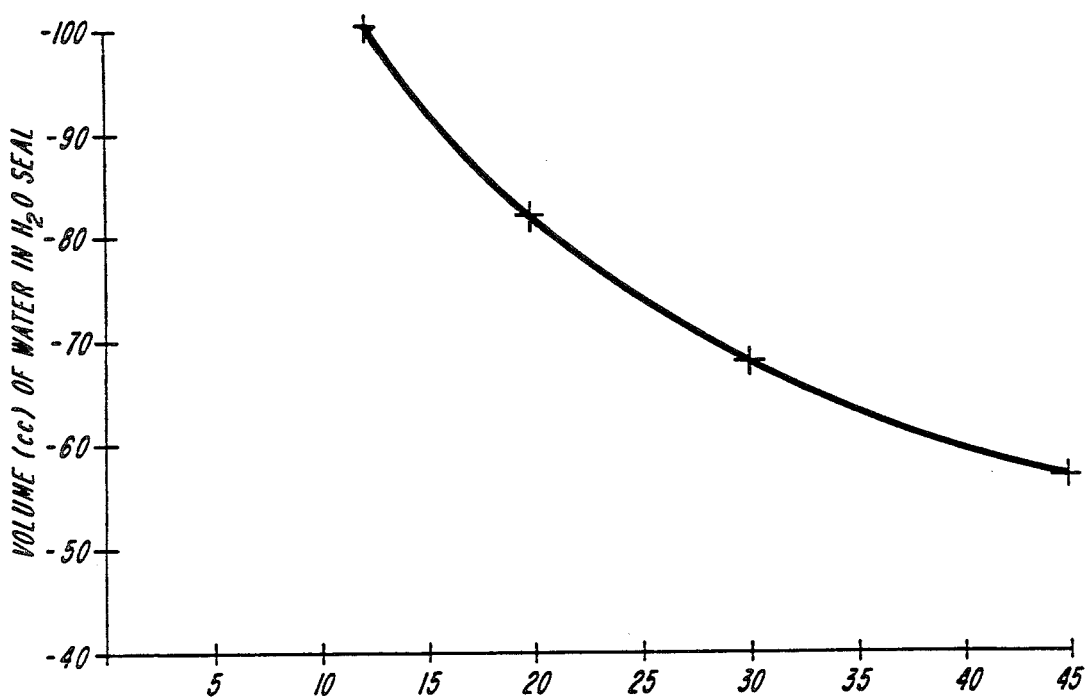
FIG. 6a is a graph representing the relationship between vacuum pressure in the collection chamber and valve release time.

FIG. 6a is a graph of the relationship between vacuum in the collection chamber 312 and the time required for the float valve 60 to release. As is shown by the graph, higher vacuum levels in the chamber 312 result in shorter release times. For purposes of illustration, assume that a normally slow breathing patient will draw 10–12 breaths per minute. By dividing the lower value of this range by a safety factor of 2 (5 breaths per minute) a maximum period of time for a held breath of 12 seconds is determined. Further, assume that at most a normally breathing patient can generate vacuum in the chamber 312 of $-90$ to $-100$ cm of water. Clearly then, to allow such an illustrative patient to breath the chest drain must allow the patient to maintain a vacuum level of $-90$ to $-100$ cm of water for a period of at most 12 seconds.

By reference to FIG. 6a, therefore, it can be seen that the float valve 60 is designed to release at 12 seconds when a vacuum of $-100$ cm of water is maintained in the collection chamber 312. As discussed above, this will allow the patient to breath. If, however, such a vacuum level is maintained for longer than 12 seconds, enough water will have passed through the notch 65 in the float valve 60 such that the water level in the column 13a supporting the ball 63 will be insufficient to maintain the ball in the seated position. The valve, therefore, will release. In this manner, dangerously high levels of vacuum that could result in damage to the patient's thoracic cavity are relieved without any nurse intervention.

Figure 6B:
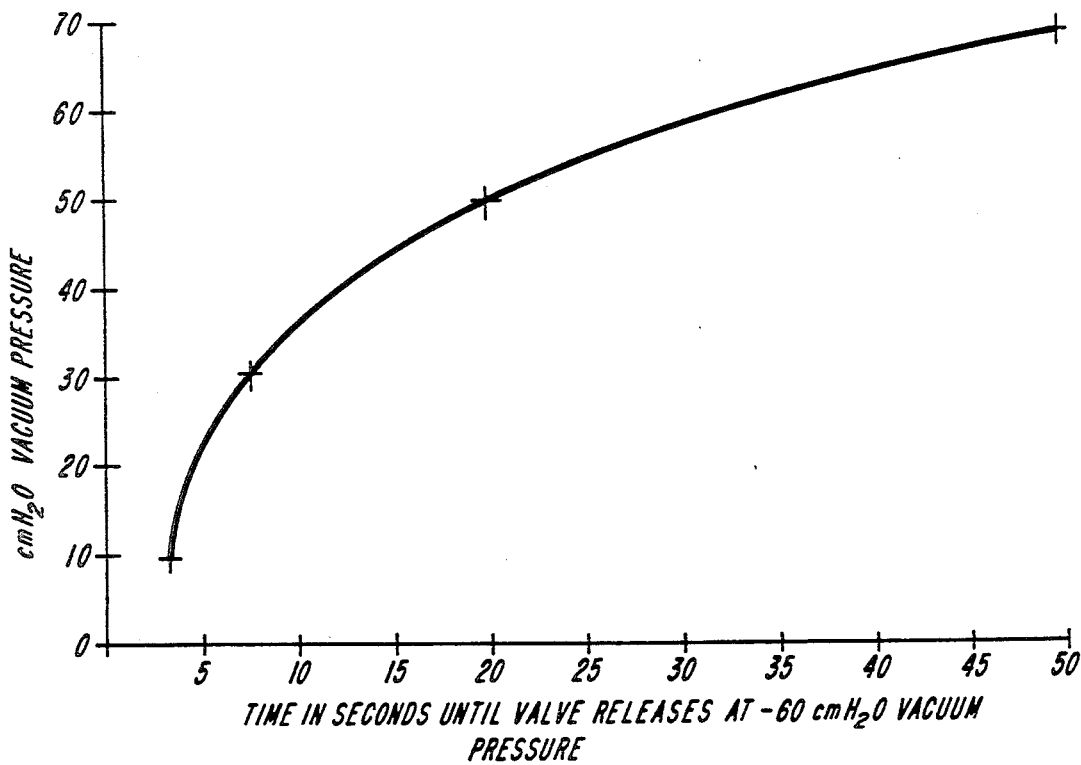
FIG. 6b is a graph representing the relationship between the volume of water in the water seal and valve release time when there is vacuum pressure in the collection chamber equal to $-60$ cm $H_2O$.

It is, therefore, an important characteristic of the present invention that the water volume in the water seal be selected to allow the float valve 60 properly release. FIG. 6b is a graph of the relationship between the volume of water in the water seal and the time required for the float 60 to release when $-60$ cm of water of vacuum is generated in the collection chamber 312. The graph shows that generally greater volumes of water in the water seal result in the float valve 60 requiring a longer period of time for release. Note that the curve asymptotically approaches a value of 70 cm of volume representing a volume of water which will result in the float valve 60 effectively never releasing.

FIG. 6b graphically illustrates that the float ball 63 is supported in the valve seat 61 by the column of water underneath it. That is, as water is drawn through the notch 65 in the valve seat 61 the water column beneath the ball 63 is depleted until it eventually can no longer support the ball in the valve seat 61. It can be understood, therefore, that larger volumes of water in the water seal will require longer periods of time to be depleted to this point, i.e. the point of valve release. In a preferred embodiment, the volume of water in the water seal chamber 313 will be between 25 and 65 cc of water. A. volume of water of approximately 40 cc has been found to be particularly effective. Accordingly, if 60 cm of water of vacuum is generated in the collection chamber 312, the float valve of 60 will release in between 5 and 50 seconds. This will be sufficient to allow a patient to breath, while prohibiting extended periods of exposure to dangerous vacuum levels. In this manner, the chest drain of the present invention is superior to known chest drains which have non-releasing check valves and require operator vacuum release through manual means.

It is also an important feature of the invention, that when the float valve 60 releases, the vacuum in the collection chamber 312 is returned to its pre-high vacuum event level. This is because no manual vent has been opened to expose the collection chamber 312 to atmospheric pressure. As a result, the amount of vacuum that the patient must generate for normal breathing will remain at acceptable levels.

The third major sub-chamber, the collection chamber portion 312, of this embodiment of the drain device is defined by the outer contours of the molded body portion 105 as well as by an internal wall 335 which extends for the entire height of the drainage device. Wall 335 separates the collection chamber 312 from water seal 313, so that the two chambers communicate only at port 319 as described above. Port 319 has a cross-sectional area of approximately one-half square centimeter in the prototype device. The total volume enclosed by the body 105, 115 of that prototype is approximately three liters, comparable to the volume of the pleural chamber. Of this amount, collection chamber 312 constitutes two or more liters. While the patient connection at port 11 is a large diameter thoracotomy tube which can transmit fairly abrupt pressure impulses to chamber 312, port 319 limits the attainable flow rates and thus modulates pressure impulses which are initiated on either side of the port.

Between the chamber-defining wall 335 and the outer side wall 336, one or more partial or complete intermediate walls 337, 338, which are integrally formed with the housing body portion 105, separate chamber 312 into sub-chambers 341, 342 and 343 as discussed below. The intermediate walls 337, 338 also support a large-area fall-through filtration element 345 below inlet 11, and extend to one or more upper wall portions 337a, 338a which provide an impoundment for fluids which have not passed through the filtration element 345.

As shown, a fluid deflector 347 spaced below the fluids inlet 11 channels the incoming fluid so that it falls straight downward into the upper portion 341a of the extreme right sub-chamber 341, onto filter 345. Filtered blood then seeps through. This fall-through filter arrangement minimizes mechanical trauma to the blood. Filtration element 345 is a large area gross filter, such as a fabric or an open-pore sponge filter, which is effective to remove clots and gross particles from the incoming fluids. It may be treated with an anticoagulating agent to pre-process the fluids passing through it. The filtered fluids then pass to the lower portion of chamber 341 where the back portion of the body angles forwardly to form a portion of lesser front-to-back depth constituting a collection sump at outlet port 19a.

When the drain receives an unusually large flow of fluids or the filter 345 becomes blocked with clots, the incoming fluids are impounded by wall 337a and eventually overflow into the space 342a between upper walls 337a and 338a. The overflow fluids contact a fresh area of the filter 345, through which they pass to chamber 342. Lower chamber 342 also communicates directly with sump region 350 and thus with the outlet port 319a.

Further, if the rate of fluid intake or amount of clots causes the impounded fluids in the space 342a to overflow, they pass over the top of wall 338a. In that event, the fluids pass without being filtered into an overflow collection sub-chamber 343 of chamber 312. The level in the filter impoundment space 342a is visible through the filter/flow status windows 136a–136f (FIG. 3), so that an excessive bleeding rate or clotting condition is easily detected by hospital personnel. The provision of an open, fall-through filter in this manner prevents back-up of fluids in the thoracotomy inlet tube from the patient, a common cause of tamponade, while still providing prefiltration of scavenged blood. This is a distinct improvement over a closed sock-type filter as used in prior art devices.

As shown in the Figure, a passage 351 is provided between chamber 343 and the sump area 350. In alternative embodiments, this passage may be omitted so that the overflow fluid is fully isolated. The windows 132, 132b (FIG. 3) may provide separate graduated fluid volume scales 132c, 132d, with the graduations on scale 132c representing the volume in chambers 341 and 342, and those of scale 132d representing the unfiltered volume in chamber 343.

Figure 14:
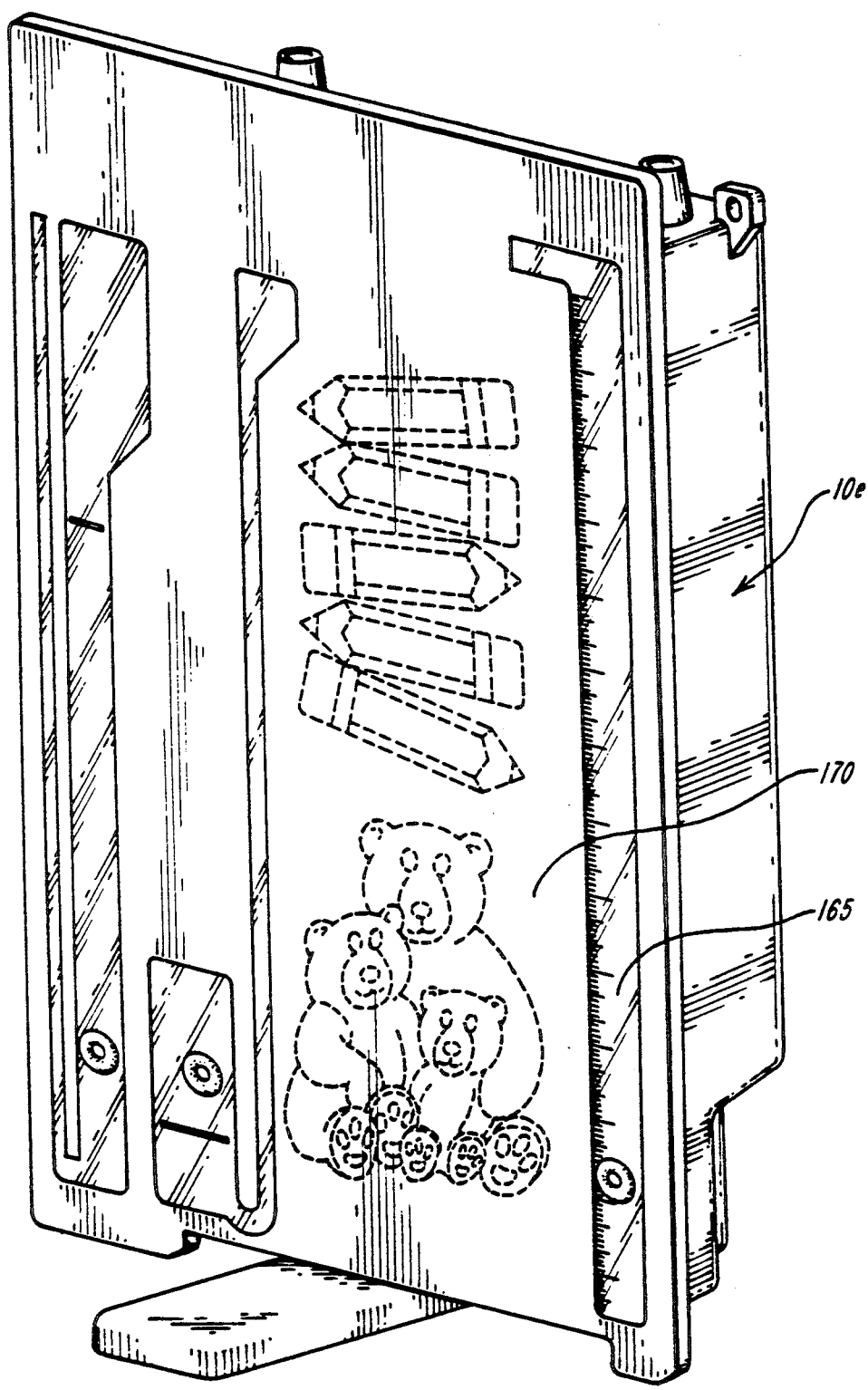
Figure 15:
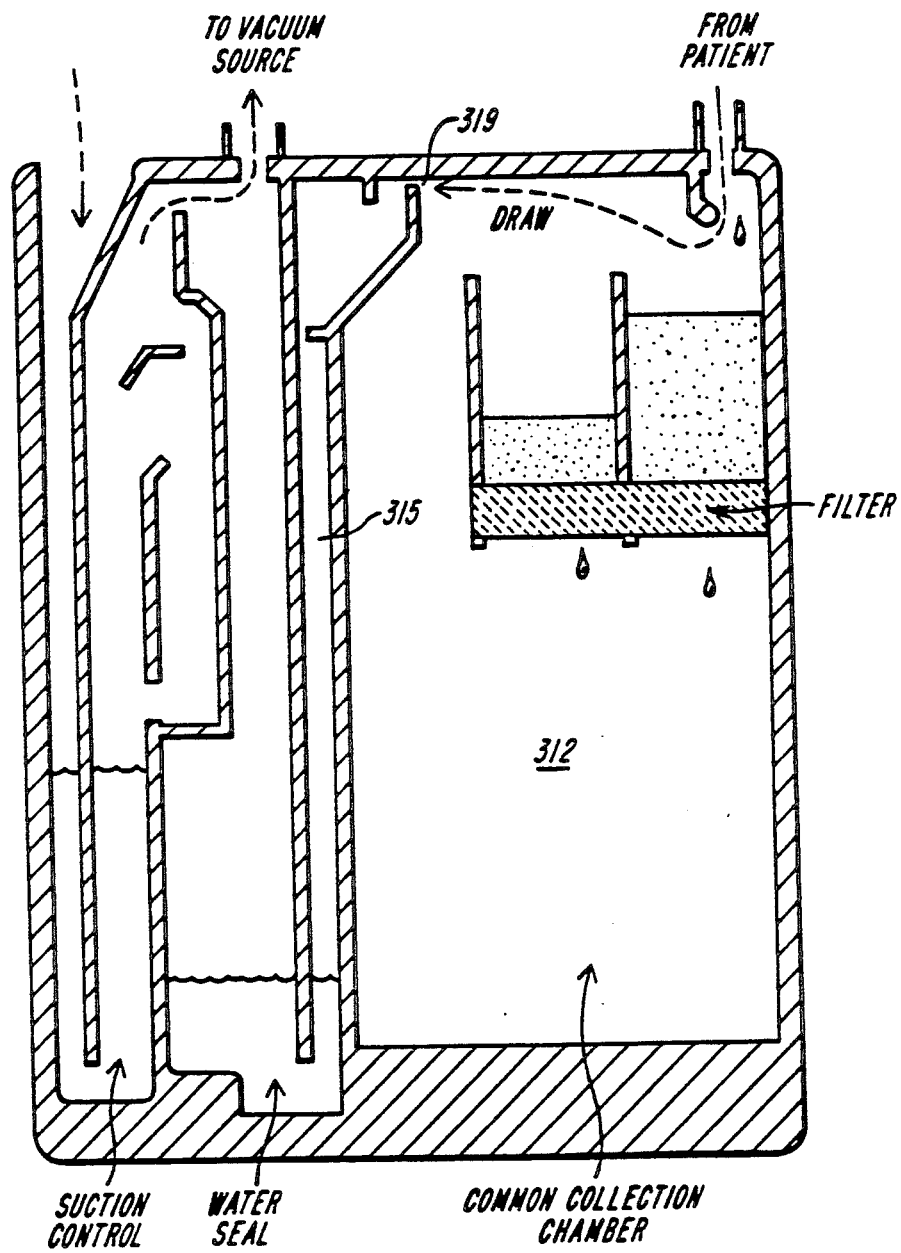
FIG. 15 illustrates interior operating characteristics of the drain device of FIGS. 5, and 7-11.

It will be seen that the structure of walls, baffles and ports just described results in the provision of a suction drain vessel wherein bidirectional pressure fluctuations are substantially compensated, and abrupt pressure impulses are modulated to more gradual perturbations that do not interrupt the functioning of the device. A further feature of note is that normal suction draws are established such that the diffusion path to the collected blood is relatively isolated. FIG. 14 illustrates the normal directions of flow in the device of FIG. 5.

From inlet 11, airflow, if any, is normally along the top of chamber 312, toward port 319. Blood entering at port 11 thus has a relatively low probability of encountering airborne contaminants, and it falls downward into chamber 341 or 342, where it is isolated from moving air. Thus, in the rare event air from water seal column 315 is drawn past port 319, it is unlikely to result in significant contamination, and the collected blood will be safe for reinfusion for at least the duration of a surgical operation or procedure.

FIG. 5 also illustrates a preferred outlet structure 185 attached to reinfusion/outlet port 19a. Port 19a is located at the lower point of the drain, and has an large bore PVC infusion tube 180 attached thereto, with a pinch clamp 21. At the end of tube 180, an IV spike port 181 having a diaphragm closure 182 and reclosable cap 183 allows the sterile connection to transfer vessel 50 or to a conventional infusion pump or line. The position of port 19a assures that collected blood is entirely drawn out, thus minimizing the risk of contamination of the collected fluid. The large bore IV tubing allows fast delivery of the collected fluid.

Figure 7:
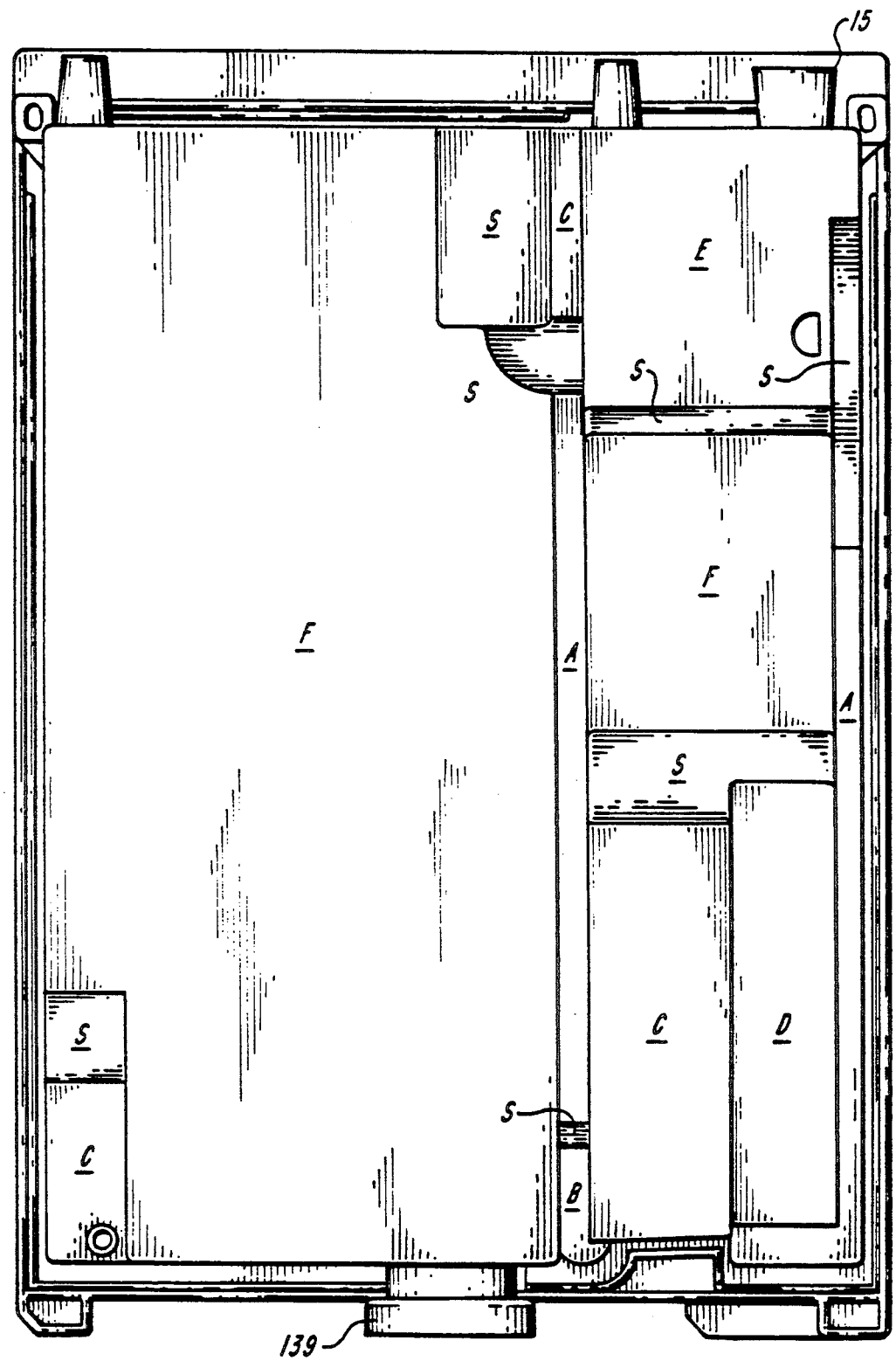
FIG. 7 is a back view of the drain device shown in the system of FIG. 3.
Figure 8:
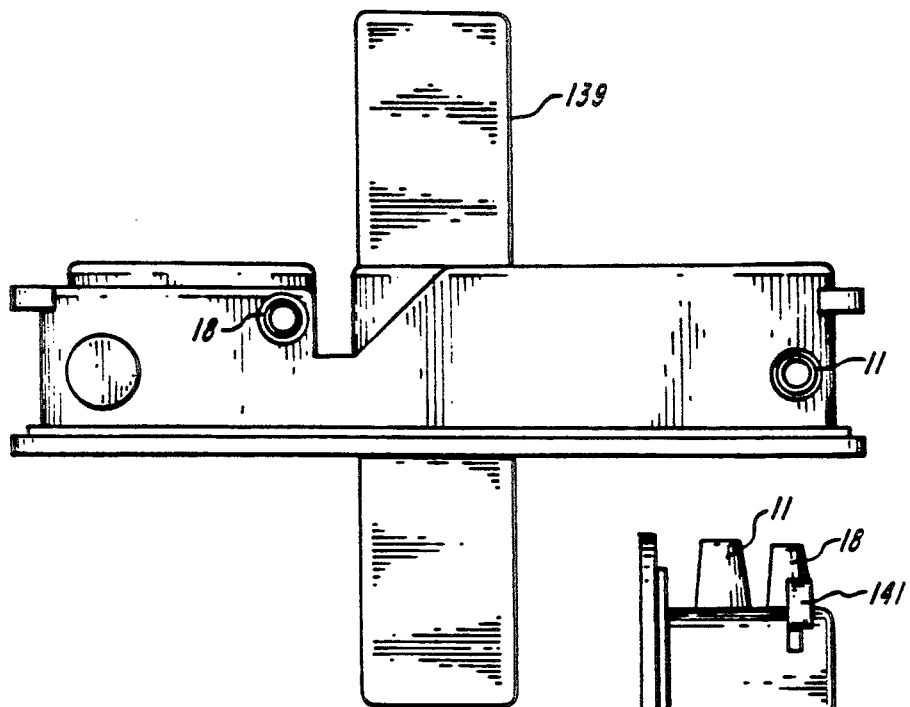
FIG. 8 is a top view of the prototype drain device of FIGS. 3 and 5.
Figure 9:
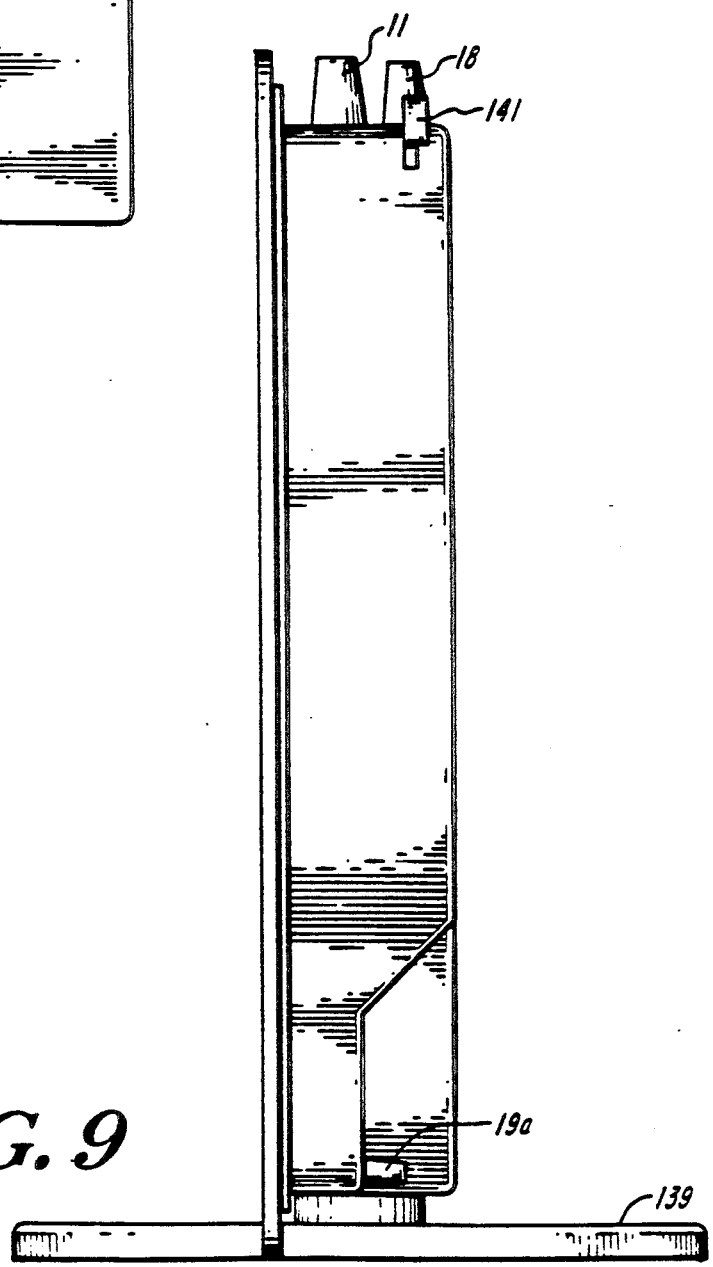
FIG. 9 is a side view from the collection chamber side of that drain device.

FIG. 7 shows a back view of the molded body portion 105 of the two-piece housing of drain 10a. The rear wall portion 105 consists of an arrangement of substantially rectangular panels each of which defines all or a portion of the rear wall of one or more of the sub-chambers or water columns described in respect of FIG. 5. In this preferred embodiment, each of the substantially rectangular panels lies parallel to the front panel at a depth "d" which is one of a few discrete values. In the illustrated prototype embodiment, which has an overall thickness or chamber depth of approximately two inches, the depth values A, B, C, D, E or F are given in the following table.

TABLE II

| Depth "d" | Inches |
|---|---|
| A | ¼ |
| B | ½ |
| C | 1 |
| D | 1¼ |
| E | 1¾ |
| F | 2 |

The regions marked "S" in FIG. 7 are slanted back wall portions which lead from one chamber depth to a different chamber depth.

This back wall structure has been found to provide a particularly advantageous set of pressure response characteristics for the columns and chambers defined thereby, as well as providing a distinctive and visually pleasing outer form quite different from the awkward box-like appearance of conventional chest drain devices.

Figure 10:
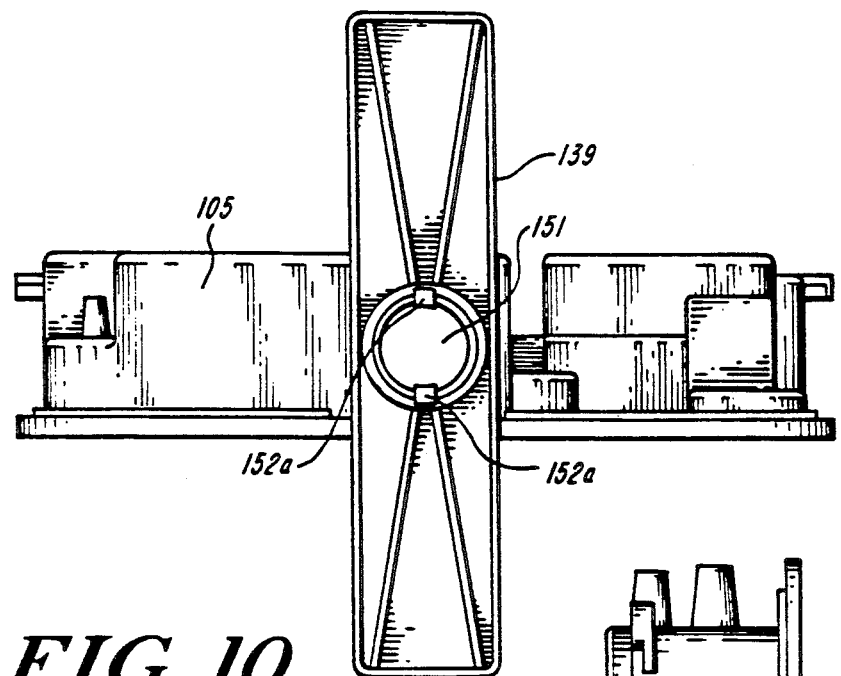
FIG. 10 is a bottom view of that drain device.
Figure 11:
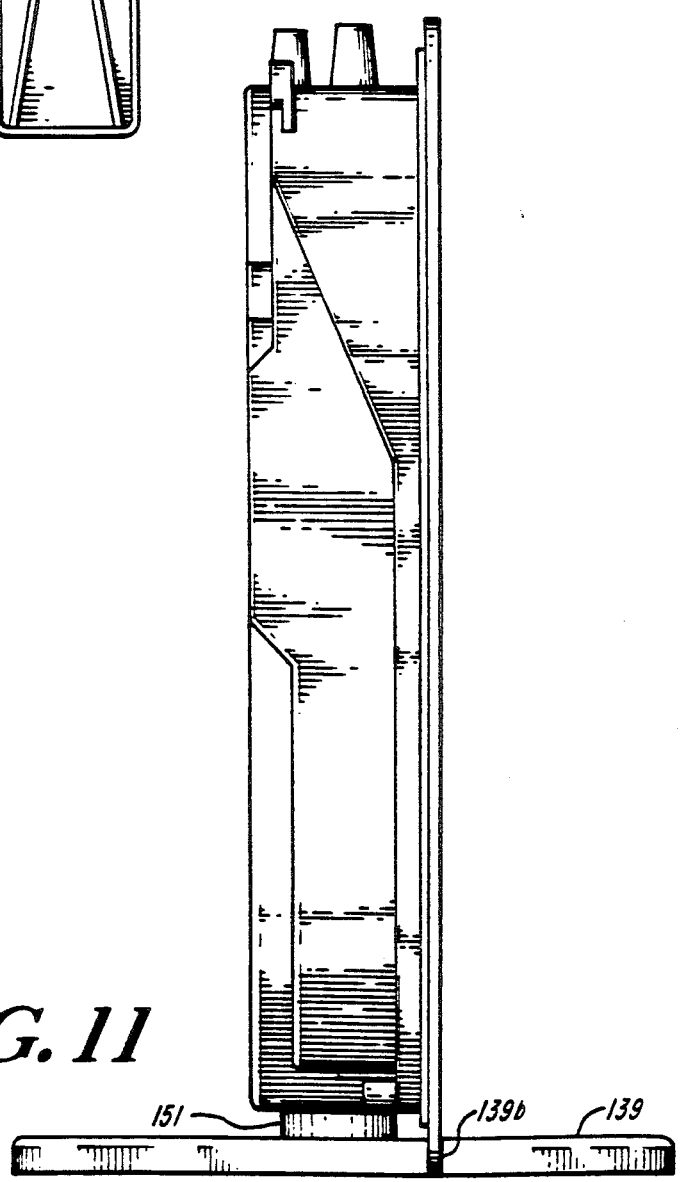
FIG. 11 is a side view from the manometer chamber side of that drain device.

FIGS. 8–11 show additional external views of the presently preferred prototype drainage device, illustrating in detail the contours and locations of the various wall, port, support and other features formed in the molded housing in this preferred construction. Among other details, these drawings show clearly the relatively large patient inlet port 11 (FIGS. 8, 9) which connects to and is preferably pre-packaged with, a large-diameter flexible latex thoracotomy tube. The transfer/infusion port 19a (FIGS. 9, 10), by contrast, connects to a smaller blood-compatible PVC tube. Preferably, the drain device is pre-packaged with a short, e.g., half-meter length of such tubing mounted on the port 19a, and having a sealed diaphragm-type spike port at its end. FIGS. 10, 11 show a cylindrical shaft 151 with stops 152a formed on the housing 105. Pedestal 139 is rotatably secured on shaft 151 by the stops, which also serve as detents to lock the pedestal perpendicular to the plane of the device when the pedestal is rotated.

Figure 12:
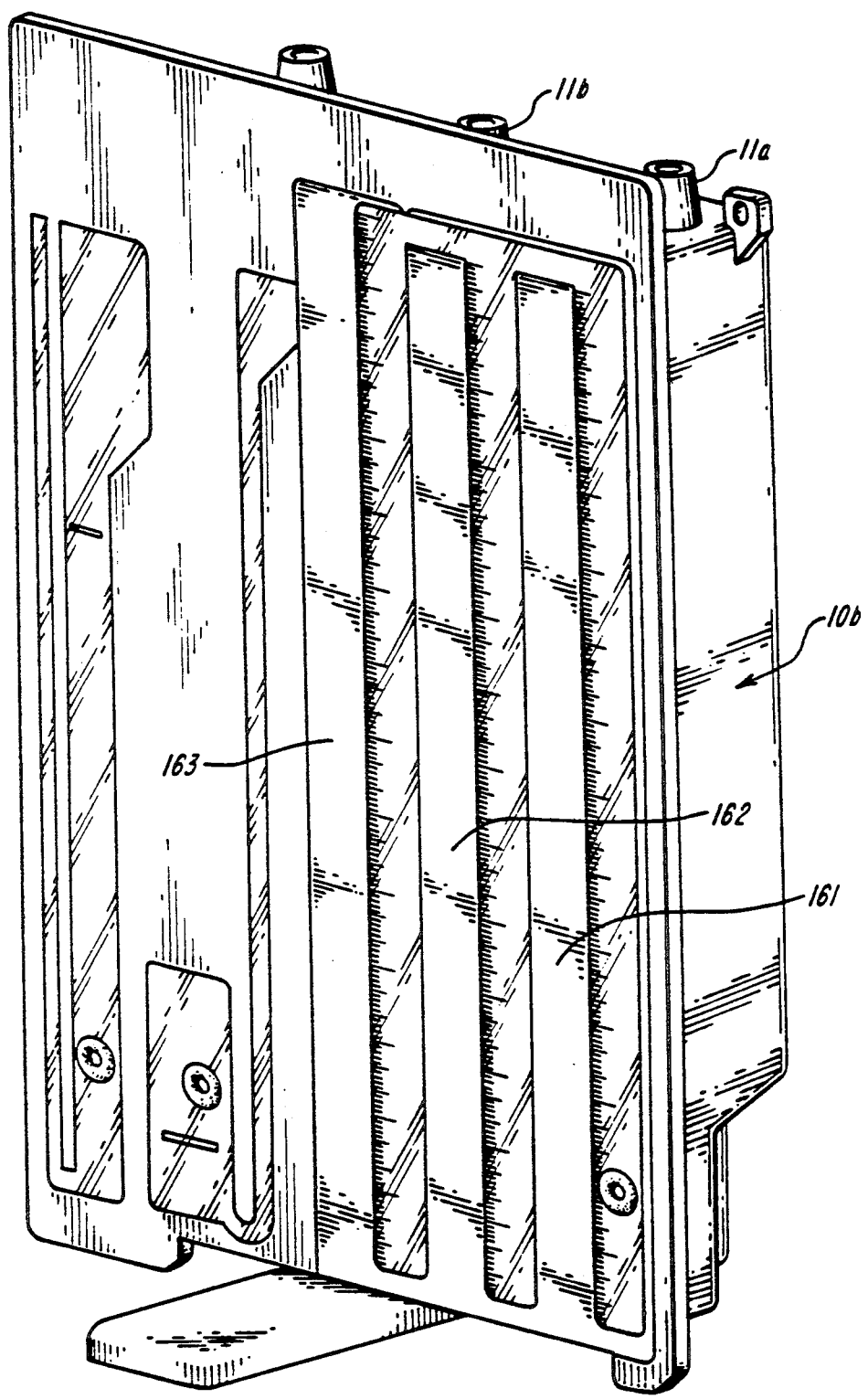
FIGS. 12, 12A, 13 and 14 are front perspective views of four different drain devices embodying different aspects of the invention.
Figure 13:
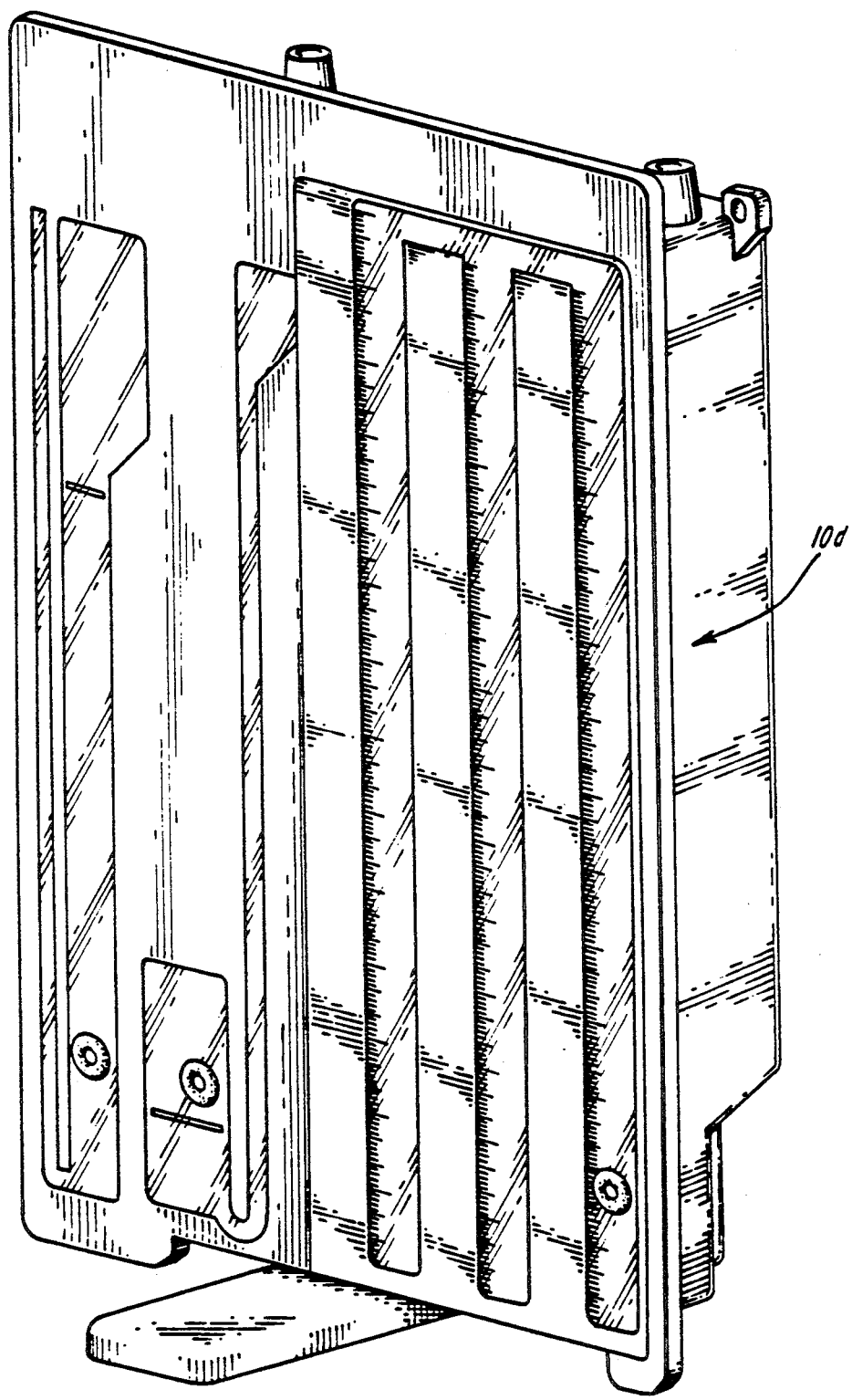

One or more of the foregoing features of the drain device are also advantageously incorporated into different drain devices illustrated in FIGS. 12–14.

FIG. 12 shows another drain device 10b which is specially adapted to collect fluids from several sites via plural patient fluid inlet ports 11a, 11b. In this device, the manometer and water seal chamber structure are substantially identical to those illustrated in FIGS. 3, 5 and 7, but the inlet ports 11a, 11b lead to different collection chambers so that the volume of fluid collected from each site may be separately ascertained from the graduated windows 161, 162, 163. In this embodiment no outlet port or gross filter is provided, and the drain serves to collect fluid and monitor collected fluid levels. It is thus not intended for fluid reinfusion. A principal collection chamber under inlet 11a has two columns located behind windows 161 and 162, respectively. A continuous wall similar to wall 337 of FIG. 5, but extending entirely to the bottom, separates the two columns and assures that first one column fills and then overflows to fill the other column. Behind window 163 a single isolated secondary collection column receives fluids only from inlet 11b, and separately indicates their volume.

Figure 12A:
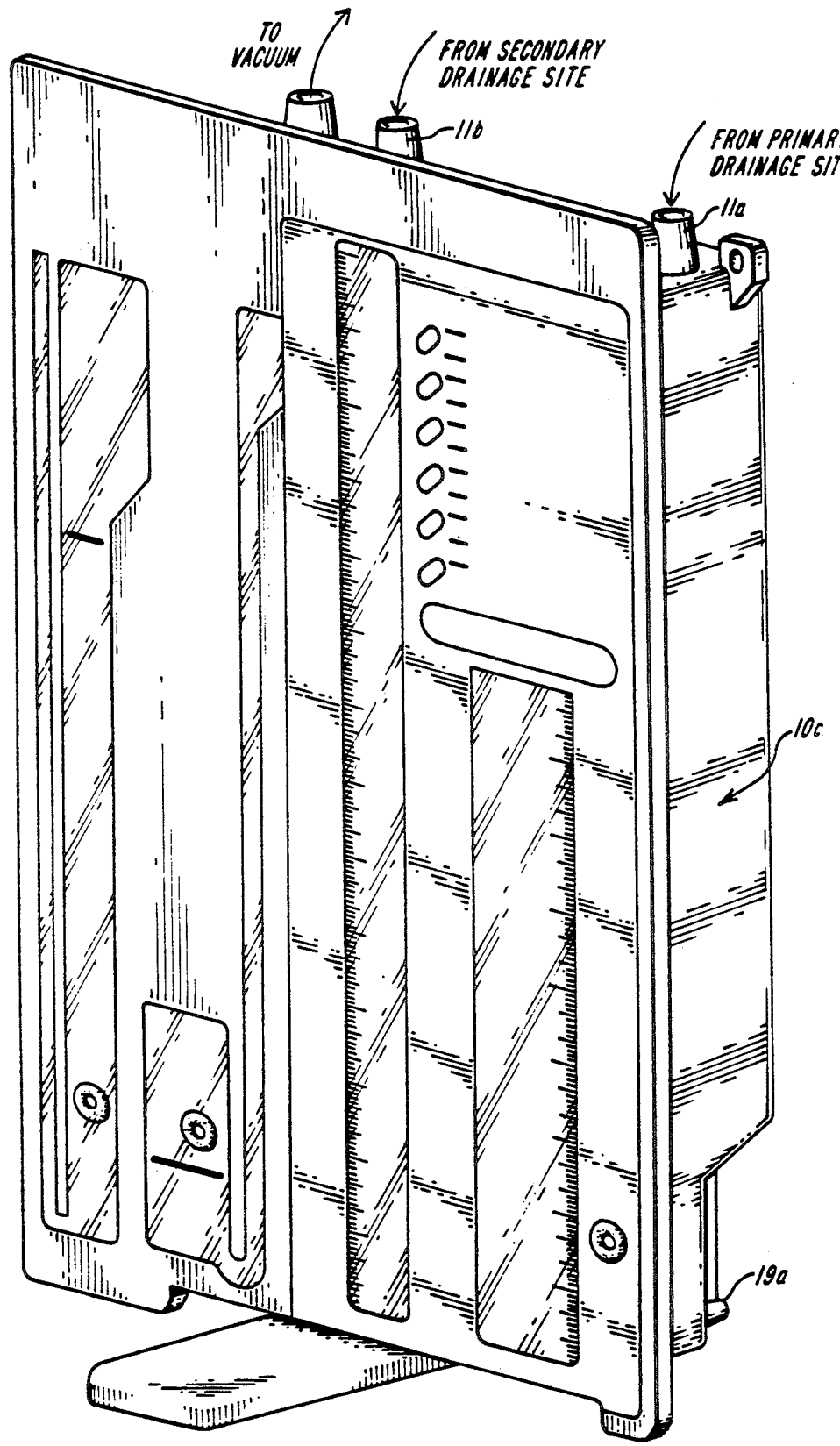

FIG. 12A shows another drain embodiment 10c having two patient inlets 11b, 11a. In this embodiment, a filter and outlet port 19a are provided for prefiltering and reinfusion of the fluid collected via inlet 11a, which is the primary inlet for mediastinal fluid drainage. Secondary inlet 11b provides unfiltered collection from a secondary site, such as one at the apex of the lung, into a preferably isolated separate graduated column.

FIG. 13 shows another drain unit 10d with a single inlet and no outlet. In this embodiment, first and second inner walls define successive overflow paths to fill first one column, then the second, then the third. Again no gross filter or fluid outlet is provided.

FIG. 14 shows another drain unit 10d according to the invention. This drain is a pediatric drain, and employs the same water column structure as the preceding devices It includes neither a gross filter nor an outlet port. The inner walls corresponding to walls 337, 338, 335 of FIG. 4 are modified to define a single collection column located behind window 165, and the column is dimensioned such that its full height corresponds to a fluids volume of only approximately two to five hundred cubic centimeters. A broad portion 170 of the panel covering the dead space between the collection column and the water seal has a bright engaging picture, represented in phantom, thereon.

Thus, the drain device described in relation to FIGS. 3, 5, and 7-11 is adapted, with minor changes of straight interior wall portions and different printing on the front face, to provide a stable and sterile suction drainage device for a variety of drain applications and autologous blood circuits.

It will be appreciated that numerous of the features shown can be used independently of others and in a variety of drain device forms and structures. It will thus be seen that a chest drain device according to the invention efficiently attains the objects set forth above as well as those made apparent from the preceding description. Since changes may be made in the illustrated device without departing from the scope of the invention, all matter contained in the above description or shown in the accompanying drawings is to be interpreted as illustrative and not in a limiting sense.

Having described the invention, what is claimed as new and secured by letters patent is:

1. A system for the collection of body fluid, comprising a collection vessel defining an interior chamber, said chamber having first, second, and third openings therein adapted for communication with the atmosphere, a hospital vacuum source, and a fluid collection tube, respectively, said chamber being subdivided to provide a buffered volume of first, second, and third successive intercommunicating sub-chambers having said respective first, second, and third openings therein,
    first and second water columns included in said first and second sub-chambers to define during normal operation first and second pressure differentials for establishing unidirectional flow from said first and third openings to said second opening while maintaining a desired subatmospheric pressure range in said third sub-chamber, said second opening being in direct fluid communication with a low pressure side of each of said first and second water columns, and
    an automatically releasing float valve positioned between said second and third sub-chambers for preventing water flow to said third sub-chamber, the float valve comprising,
        a float having a density less than one and being positioned in a fluid path of said second sub-chamber, and
        a valve seat disposed above said float, said valve seat defining an aperture having a maximum dimension smaller than the outer dimension of said float, said aperture being
        shaped so that when, due to a negative pressure condition in said third sub-chamber, the water level in said second sub-chamber rises to cause said float to be seated in said aperture, a quantity of water can still pass therethrough into an impound volume, said valve seat being positioned at a height in relation to the volume of water in said second water column such that water passing through said aperture depletes said water column and it no longer supports said float in said aperture thereby causing said float valve to release.

2. A system as set forth in claim 1 wherein said float is a ball and said aperture is substantially circular.

3. A system as set forth in claim 1 further comprising,
    a fourth opening in communication with said third sub-chamber, and
    means for drawing fluid from said third sub-chamber.

4. A system as set forth in claim 3, wherein said fourth opening is a closable outflow opening in a lower wall of said third sub-chamber.

5. A system as set forth in claim 4 wherein the negative pressure condition is generated by fluid being drawn out of said third sub-chamber.

6. A system as set forth in claim 1 wherein said aperture has a bevelled edge.

7. A system as set forth in claim 2 wherein said aperture is shaped as a circle in communication with a notch.

8. A system as set forth in claim 1 wherein said valve seat is disposed so that when the fluid level causes said float to be seated in said aperture, a column of water approximately 25 cm high is positioned below said valve seat.

9. A system as set forth in claim 1 wherein the volume of said second water column is between approximately 25 cc and 70 cc.

10. A system as set forth in claim 1 wherein the volume of said second water column is approximately 40 cc.

11. A system as set forth in claim 10 wherein, said float valve is constructed to release when said third sub-chamber is exposed to vacuum equivalent to approximately $-90$ cc of $H_2O$ for a period longer than approximately two breath intervals.

12. A system as set forth in claim 1, wherein the volume of water in said second sub-chamber is such that said float valve will release within a period of approximately two breath intervals when a Pressure equivalent to approximately $-90$ cc of $H_2O$ is generated in said third sub-chamber.

13. A system as set forth in claim 3, further comprising, a fluid transfer vessel, and means for releasably interconnecting said fluid transfer vessel and said fourth opening of said third sub-chamber to receive collected fluid therefrom.

14. A system as set forth in claim 13, wherein said system is a system for collection and infusion of autologous blood.

15. A system as set forth in claim 1, wherein said body fluid is blood, and further comprising a fall-through filter in said third sub-chamber below said third opening.

16. A system as set forth in claim 1, wherein said second sub-chamber defines a lower narrow portion and an upper wide portion, said float valve being disposed in said upper wide portion.

17. A system as set forth in claim 16, wherein said lower narrow portion has a width smaller than the outer dimension of said float thereby acting as a stop to position the ball adjacent the valve seat.

18. A system for combined collection and infusion of body fluid, comprising a collection vessel defining an interior chamber, said chamber having first, second, and third openings therein adapted for communication with the atmosphere, a hospital vacuum source, and a fluid collection tube, respectively, said chamber being subdivided to provide a buffered volume of first, second, and third successive intercommunicating sub-chambers having said respective first, second, and third openings therein, first and second water columns included in said first and second sub-chambers to define during normal operation first and second pressure differentials for establishing unidirectional flow from said first and third openings to said second opening while maintaining a desired subatmospheric pressure range in said third sub-chamber, said second opening being in direct fluid communication with a low pressure side of each of said first and second water columns, a fourth opening in communication with said third sub-chamber, a fluid transfer vessel, means for releasably interconnecting said fluid transfer vessel and said fourth opening of said third sub-chamber to receive collected fluid therefrom means for withdrawing blood from said third sub-chamber into said fluid transfer vessel, and an automatically releasing float valve positioned between said second and third sub-chambers for preventing water flow to said third subchamber, the float valve comprising, a float having a density less than one and being positioned in a fluid path of said second sub-chamber, and a valve seat disposed above said float, said valve seat defining an aperture having a maximum dimension smaller than the outer dimension of said float, said aperture being shaped so that when, due to a negative pressure condition in said third sub-chamber, the water level in said second sub-chamber rises to cause said float to be seated in said aperture, said float substantially but not entirely obstructs said aperture so that a bypass quantity of water passes therethrough into an impound volume, said bypass volume being a function of pressure such that for an excessive negative pressure said bypass volume depletes said water column sufficiently such that the water column no longer supports said float in said aperture thereby causing said float valve to release.

19. A system as set forth in claim 18 wherein said float is a ball and said aperture is substantially circular.

20. A system as set forth in claim 18, wherein said fourth opening is a closable outflow opening in a lower wall of said third sub-chamber.

21. A system as set forth in claim 18 wherein the negative pressure condition is generated by fluid being drawn out of said third sub-chamber.

22. A system as set forth in claim 18 wherein said aperture has a bevelled edge.

23. A system as set forth in claim 19 wherein said aperture is shaped as a circle in communication with a notch.

24. A system as set forth in claim 18 wherein said valve seat is disposed so that when the fluid level causes said float to be seated in said aperture, a column of water 25 cm high is positioned below said valve seat.

25. A system as set forth in claim 18 wherein the volume of said second water column is between approximately 25 cc and 65 cc.

26. A system as set forth in claim 18 wherein the volume of said second water column is approximately 40 cc.

27. A system as set forth in claim 26 wherein, said float valve is constructed to release when said third sub-chamber is exposed to vacuum equivalent to approximately $-90$ cc of $H_2O$ for at least approximately 12 seconds.

28. A system as set 'forth in claim 18, wherein the volume of water in said second sub-chamber is such that said float valve will release in approximately 12 seconds when a pressure equivalent to approximately $-90$ cc of $H_2O$ is generated in said third sub-chamber.

29. A system as set forth in claim 18, wherein said body fluid is blood, and further comprising a fall-through filter in said third sub-chamber below said third opening.

30. A system as set forth in claim 18, wherein said second sub-chamber defines a lower narrow portion and an upper wide portion, said float valve being disposed in said upper wide portion.

31. A system as set forth in claim 30, wherein said lower narrow portion is of a width smaller than the outer dimension of said float.

32. A system as set forth in claim 18, wherein said system is a system for collection and infusion of autologous blood.

33. A system for the collection of body fluid, comprising a collection vessel defining an interior chamber, said chamber having first, second, and third openings therein adapted for communication with the atmosphere, a hospital vacuum source, and a fluid collection tube, respectively, said chamber being subdivided to provide a buffered volume of first, second, and third successive intercommunicating sub-chambers having said respective first, second, and third openings therein, first and second water columns included in said first and second sub-chambers to define during normal operation first and second pressure differentials for establishing unidirectional flow from said first and third openings to said second opening while maintaining a desired subatmospheric pressure range in said third sub-chamber, said second opening being in direct fluid communication with a low pressure side of each of said first and second water columns, and an automatically releasing valve positioned between said second and third sub-chambers for freely permitting air flow while impeding water flow to said third sub-chamber, the valve being positioned at a height in relation to the volume of water in said second water column such that when a negative Pressure condition is maintained in said third sub-chamber for longer than a predetermined period of time, substantially the entire volume of water in said second sub-chamber passes through said valve so that air freely passes from said second sub-chamber to said third sub-chamber.

34. A system as set forth in claim 33 wherein the volume of water in said second sub-chamber is such that said determined period of time is equivalent to approximately two breath-intervals when said third sub-chamber is exposed to vacuum equivalent to approximately $-90$ cc of $H_2O$.

35. A system as set forth in claim 33 wherein said valve is a porous hydrophobic filter.

36. A system as set forth in claim 33 wherein the volume of said second water column is between approximately 25 cc and approximately 65 cc.

37. A system as set forth in claim 33 wherein the volume of said second water column is approximately 40 cc.

38. A system as set forth in claim 37 wherein said predetermined period of time is equivalent to approximately two breath-intervals when said third sub-chamber is exposed to vacuum equivalent to approximately $-90$ cc of $H_2O$.

39. A system as set forth in claim 35 wherein said filter has a cross-sectional area of from approximately 1 $cm^2$ to approximately 20 $cm^2$.

40. A system as set forth in claim 35 wherein said filter defines pores having a diameter from approximately ½ micron to approximately 100 microns.

* * * * *

UNITED STATES PATENT AND TRADEMARK OFFICE
CERTIFICATE OF CORRECTION

PATENT NO. : 5,114,416

DATED : May 19, 1992

INVENTOR(S) : Karwoski et al.

Page 1 of 2

It is certified that error appears in the above-identified patent and that said Letters Patent is hereby corrected as shown below:

Column 4, line 31, delete "Patient" and insert --patient--.

Column 7, line 35, after "113d" delete ".".

Column 7, line 46, delete "Passing" and insert --passing--.

Column 10, line 3, delete "Patient" and insert --patient--.

Column 10, line 43, after "securely" insert --.--.

Column 10, line 66, after "filter" insert --,--.

Column 10, line 67, after "chamber" insert --.--.

Column 11, line 1, delete "certains" and insert --contains--.

Column 17, line 25, after "devices" insert --.--.

UNITED STATES PATENT AND TRADEMARK OFFICE
CERTIFICATE OF CORRECTION

PATENT NO. : 5,114,416
DATED : May 19, 1992
INVENTOR(S) : Karwoski et al.

It is certified that error appears in the above-identified patent and that said Letters Patent is hereby corrected as shown below:

column 18, line 64, delete "Pressure" and insert --pressure--.

column 21, lines 2-3, delete "Permitting" and insert --permitting--.

column 21, line 7, delete "Pressure" and insert --pressure--.

Signed and Sealed this

Thirty-first Day of August, 1993

Attest:

BRUCE LEHMAN

*Attesting Officer*     *Commissioner of Patents and Trademarks*